US007057086B2

(12) United States Patent
Vaughan et al.

(10) Patent No.: US 7,057,086 B2
(45) Date of Patent: Jun. 6, 2006

(54) THERAPEUTIC METHODS EMPLOYING PAI-1 INHIBITORS AND TRANSGENIC NON-HUMAN ANIMAL FOR SCREENING CANDIDATE PAI-1 INHIBITORS

(75) Inventors: Douglas E. Vaughan, Nashville, TN (US); Mesut Eren, Nashville, TN (US); Paul J. Declerck, Leuven (BE)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 10/368,995

(22) Filed: Feb. 19, 2003

(65) Prior Publication Data

US 2003/0217371 A1 Nov. 20, 2003

Related U.S. Application Data

(60) Provisional application No. 60/358,061, filed on Feb. 19, 2002.

(51) Int. Cl.
*A01K 67/027* (2006.01)
*G01N 33/00* (2006.01)
*C07H 21/04* (2006.01)
*C12N 15/00* (2006.01)

(52) U.S. Cl. .......................... 800/18; 800/3; 536/24.1; 435/320.1

(58) Field of Classification Search .................... 800/3, 800/13, 18; 536/23.5, 24.1; 435/320.1
See application file for complete search history.

(56) References Cited

U.S. PATENT DOCUMENTS 5,422,245 A 6/1995 Nielsen et al.
5,980,938 A 11/1999 Berg et al.

FOREIGN PATENT DOCUMENTS

WO  WO 90/13648  11/1990

OTHER PUBLICATIONS

Hammer et al. Genetic engineering of mammalian embryos. J. Anim. Sci. 63:269-278, 1986.*
Ebert et al. A Moloney MLV-rat somatotropin fusion gne produces biologically active somatotropin in a transgenic pig. Molecular Endocrinology 2:277-283, 1988.*
Strojek et al. The use of transgenic animal techniques for livestock improvement. In: Genetic Engineering: Principles and methods, vol. 10, pp. 221-246, 1988.*
Kappel et al. Regulating gene expression in trangenic animals. Current Opinion in Biotechnology 3:548-553, 1992.*
Mullins et al. Perspective Series: Molecular medicine in genetically engineered animals. J. Clin. Invest. 98: S37-S40, 1996.*
Wall, R.J. Transgenic livestock: Progress and prospects for the future. Theriogenology 45:57-68, 1996.*
Lijnen et al. Nutritionally induced obesity is attenuated in transgenic mice overexpressing plasminogen activator inibitor-1.*
Harats et al. Targeting gene expression to the vascular wall in transgenic mice using the murine preproendothelin-1 promoter. J. Clin. Invest. 95:1335-1344, 1995.*
Erickson et al., Development of venous occlusions in mice transgenic for the plasminogen activator inhibitor-1 gene, *Nature* 346:74-76 (Jul. 5, 1990).
Lyons-Giordano et al., Skin Abnormalities in Mice Transgenic for Plasminogen Activator Inhibitor 1: Implications for the Regulation of Desquamation and Follicular Neogenesis by Plasminogen Activator Enzymes, *Development of Biology* 170:289-298 (1995).
Eitzman et al., Bleomycin-induced Pulmonary Fibrosis in Transgenic Mice That either Lack or Overexpress the Murine Plasminogen Activator Inhibitor-1 Gene, *J. Clin. Invest.* 97(1):232-237 (Jan. 1996).
Yamazaki et al., "Hair Cycle-Dependent Expression of Hepatocyte Growth Factor (HGF) Activator, Other Proteinases, and Proteinase Inhibitors correlates with the Expression of HGF in Rat Hair Follicles" *Journal for Investigative Dermatology Symposium Proceedings*, 4: 312-315, 1999.
Vleugels et al., "Evaluation of the Mechanism of Inactivation of Plasminogen Activator Inhibitor-1 by Monoclonal Antibodies Using a Stable Variant", *Fibrinolysis & Proteolysis* . 12 (5): 277-282, 1998.
Pannekoek et al., "Endothelial Plasminogen Activator Inhibitor (PAI): A New Member of the Serpin Gene Family" *The EMPO Journal*, 5(10): 2539-2544, 1986.
Eren et al., "Structure/Function Relationships and Phenotype in PAI-1 Transgenic Mice", *Circulation*, 106(19) Supplement: II-40, Nov. 5, 2002.

\* cited by examiner

*Primary Examiner*—David Guzo
*Assistant Examiner*—Quang Nguyen
(74) *Attorney, Agent, or Firm*—Jenkins, Wilson & Taylor, P.A.

(57) ABSTRACT

A method of testing a candidate composition for PAI-1 inhibition activity is disclosed. The method includes the steps of obtaining a transgenic non-human warm blooded vertebrate animal having incorporated into its genome a PAI-1 gene encoding a biologically active PAI-1 polypeptide, the PAI-1 gene being present in the genome in a copy number effective to confer over-expression in the transgenic non-human animal of the PAI-1 polypeptide; administering the composition to the transgenic non-human animal; and observing the transgenic non-human animal for determination of a change in the transgenic non-human animal indicative of inhibition of the activity of PAI-1. A transgenic non-human animal useful in such a method is also disclosed, as is a PAI-1 transgene construct encoding a biologically active PAI-1 polypeptide useful for preparing the transgenic non-human animal.

8 Claims, 3 Drawing Sheets

Construction of the Stable PAI-1 Transgene: The stable human PAI-1 gene was cloned into a plasmid containing the mouse preproendothelin-1 (mPPET-1) gene promoter (5.9 kb). Xho I-Not I Fragment of p5.9-PAI-1.stab was used for microinjections to generate the transgenic mouse.

PAI-1 Transgenic Mice Exhibit an Altered Cutaneous Phenotype as Compared to Wild-Type Mice. The Extent of Epidermal Phenotype due to the Overexpression of Stable PAI-1 Gene is Dose-Dependent in Homozygous (left) and Hemizygous (right) Transgenic Mice Compared to the Wild-Type Mouse (center).

Hemotoxylin and Eosin Stained Spleen Sections from Wild-Type and Transgenic Mice

```
                         SEQUENCE LISTING

<160> NUMBER OF SEQ ID NOS: 16

<210> SEQ ID NO 1
<211> LENGTH: 2970
<212> TYPE: DNA
<213> ORGANISM: Cow
<220> FEATURE:
<221> NAME/KEY: CDS
<222> LOCATION: (122)..(1330)
<223> OTHER INFORMATION:

<400> SEQUENCE: 1
gcaaagagca ccgtccagag agagccacac ctccttttca gtggaggaag ggctaccacc      60
gtcaacaccc gcagcggcag caggaacaaa ccgcccatcc caaggcactg cgaaattcag     120 g atg cgg atg tct ccg gtc ttt gcc tgc ctc gcc ctg ggc ctg gcc ctc    169
  Met Arg Met Ser Pro Val Phe Ala Cys Leu Ala Leu Gly Leu Ala Leu
  1               5                  10                  15 atc ttt ggt gaa ggg tct gcc tcc tac cag ccc cag tct gcg gcg gcc       217
Ile Phe Gly Glu Gly Ser Ala Ser Tyr Gln Pro Gln Ser Ala Ala Ala
                20                  25                  30 agc ctg gcc aca gac ttt gga gtg aag gtg ttt cag cag gtg gtg cgg       265
Ser Leu Ala Thr Asp Phe Gly Val Lys Val Phe Gln Gln Val Val Arg
            35                  40                  45 gcc tcc aag gac cgc aac gtg gtt ttc tca ccc tat ggg gtg gcc tca       313
Ala Ser Lys Asp Arg Asn Val Val Phe Ser Pro Tyr Gly Val Ala Ser
        50                  55                  60 gtc ctg gcc atg ctg cag ctg acc aca gga gga gaa acc cgc cag cag       361
Val Leu Ala Met Leu Gln Leu Thr Thr Gly Gly Glu Thr Arg Gln Gln
65                  70                  75                  80 atc caa gag gca atg caa ttc aag att gaa gag aag ggc atg gcc cct       409
Ile Gln Glu Ala Met Gln Phe Lys Ile Glu Glu Lys Gly Met Ala Pro
                85                  90                  95 gcc ttc cac cga ctg tac aag gag ctc atg ggc ccg tgg aac aag gat       457
Ala Phe His Arg Leu Tyr Lys Glu Leu Met Gly Pro Trp Asn Lys Asp
            100                 105                 110 gag atc agc aca gcc gat gcc atc ttc gtg cag cgg gac cta gag ctg       505
Glu Ile Ser Thr Ala Asp Ala Ile Phe Val Gln Arg Asp Leu Glu Leu
        115                 120                 125 gtc cat ggt ttc atg ccc aac ttc ttc agg ctg ttc cgt acc acg gtc       553
Val His Gly Phe Met Pro Asn Phe Phe Arg Leu Phe Arg Thr Thr Val
    130                 135                 140 aag cag gtt gac ttc tct gaa gtg gag aga gcc agg ttc atc gtc aac       601
Lys Gln Val Asp Phe Ser Glu Val Glu Arg Ala Arg Phe Ile Val Asn
145                 150                 155                 160 gac tgg gtg aaa aga cac aca aaa ggc atg atc agc gac tta ctt ggt       649
Asp Trp Val Lys Arg His Thr Lys Gly Met Ile Ser Asp Leu Leu Gly
                165                 170                 175 gaa ggg gct gtg gac cag ctg aca cgc ctg gtc ctg gta aat gcc ctc       697
Glu Gly Ala Val Asp Gln Leu Thr Arg Leu Val Leu Val Asn Ala Leu
            180                 185                 190 tac ttc aac ggc cag tgg aag atg ccc ttc cca gag tca aac acc cac       745
Tyr Phe Asn Gly Gln Trp Lys Met Pro Phe Pro Glu Ser Asn Thr His
        195                 200                 205 cac cgc ctc ttc cac aag tcc gat ggc agc acc atc tct gtg ccc atg       793
His Arg Leu Phe His Lys Ser Asp Gly Ser Thr Ile Ser Val Pro Met
    210                 215                 220 atg gct cag acc aac aag ttc aac tac act gag ttt acc acc ccc gac       841
Met Ala Gln Thr Asn Lys Phe Asn Tyr Thr Glu Phe Thr Thr Pro Asp
225                 230                 235                 240
```

| | | |
|---|---|---|
| ggc cgt tac tac gac atc ctg gaa ttg ccc tac cac ggg aac act ctc<br>Gly Arg Tyr Tyr Asp Ile Leu Glu Leu Pro Tyr His Gly Asn Thr Leu<br>245 250 255 | | 889 |
| agc atg ctc att gct gcc ccc tat gag aag gag gtg ccg ctc tct gcc<br>Ser Met Leu Ile Ala Ala Pro Tyr Glu Lys Glu Val Pro Leu Ser Ala<br>260 265 270 | | 937 |
| ctc acc agc att ctg gat gct gag ctc atc agc cag tgg aaa ggg aat<br>Leu Thr Ser Ile Leu Asp Ala Glu Leu Ile Ser Gln Trp Lys Gly Asn<br>275 280 285 | | 985 |
| atg acc agg ctg acc cgc ctc ctg gtt ctg ccc aag ttc tcc ctg gag<br>Met Thr Arg Leu Thr Arg Leu Leu Val Leu Pro Lys Phe Ser Leu Glu<br>290 295 300 | | 1033 |
| acc gaa atc gac ctc agg agg ccg ctg gag aat ttg gga atg acc gac<br>Thr Glu Ile Asp Leu Arg Arg Pro Leu Glu Asn Leu Gly Met Thr Asp<br>305 310 315 320 | | 1081 |
| atg ttt agg ccg agc cag gcg gac ttc tcc agt ttt tca gat caa gag<br>Met Phe Arg Pro Ser Gln Ala Asp Phe Ser Ser Phe Ser Asp Gln Glu<br>325 330 335 | | 1129 |
| ttt ctg tac gtg tcg cag gcg ctg cag aag gtg aag att gag gtg aat<br>Phe Leu Tyr Val Ser Gln Ala Leu Gln Lys Val Lys Ile Glu Val Asn<br>340 345 350 | | 1177 |
| gag agc ggc acg ctg gcg tcc tcc tcc aca gcc ctt gta gtc tca gcc<br>Glu Ser Gly Thr Leu Ala Ser Ser Ser Thr Ala Leu Val Val Ser Ala<br>355 360 365 | | 1225 |
| cga atg gcc ccc gag gag atc atc atg gac aga ccc ttc ctc ttc gtg<br>Arg Met Ala Pro Glu Glu Ile Ile Met Asp Arg Pro Phe Leu Phe Val<br>370 375 380 | | 1273 |
| gtg cgg cac aat ccc aca gga act gtc ctg ttc atg ggc caa gtg atg<br>Val Arg His Asn Pro Thr Gly Thr Val Leu Phe Met Gly Gln Val Met<br>385 390 395 400 | | 1321 |
| gaa ccc tga ccatggggaa ggcagccctc atctgggaca gaatggagat<br>Glu Pro | | 1370 |
| gtccaagagg aagaaagtcc ggagcaaaga attttatta attcattttt ctggaaaaag | | 1430 |
| agaagatgtt tatttattta tttttccatg gtaaattctt ttgaatctgc ctcttagacc | | 1490 |
| taactttggg ctctctcagg aggggcaaag aggacctttg agttaaaccc tccaatggag | | 1550 |
| accctgggaa agactgggag gcataacacc cagccggcct cccaactgga ctgtaggact | | 1610 |
| cccaggactg ctggcccagc tgcttctgcc catcgttctg cctggttcgg ttttgggtcc | | 1670 |
| tggatcccac cgaggccctg gtaggatggc accacaaggc ctacatgaag gagcttttgt | | 1730 |
| gtgttcacta gaaatgtgtg ttccggtcac gttgctgtca ttcttgcact gtctgccact | | 1790 |
| gctgagaagg ctggcagcag gcccgagaag gccaaggcga aaacaccct ttcatgccaa | | 1850 |
| ggtccatctg tccccagctc cgaggtttga gacccaccca ggcctggctg ctccctcccc | | 1910 |
| aggaaacagt gtgtatatat tattttagag tgtagatgac ttgtttactc agagaagcag | | 1970 |
| gtttctgctt cccacaaact ttatgttgca gaaacgcaag gagagacaag gtgtgtgcct | | 2030 |
| ggttctttgg ctcccatctc ctggtgggga gggtgagatg ccagggtgt gcctgaatat | | 2090 |
| ttatcacatc cttgtccttg tgtgcttggg agaaagaaag gtctactgag aaaacagatt | | 2150 |
| atttagcctt gttcaccgtg ttccctttgg ggggtctgtg tcgccgcatc tcaggagagg | | 2210 |
| cctcttgact gtccctcccc tccaccaggt ggcaagcctc ccggggccca cactgccacc | | 2270 |
| tggcggaggc ccagcgcccc cgcgcctctc ctttcctcga ttttccaccc gatggagccg | | 2330 |
| cgtccctggc aggaccatcc aacttcggct cacttttagg gaccgaaagg atgtggtggg | | 2390 |
| tgaagggaga cggagtggtt tcaaaatttt ccagtatatt taggagcggg agtgcaaggg | | 2450 |

```
gctccacgac ctagcaggac agaactttcc ccaattacag ggtgactcac agccgcactg    2510
gtgactcatt tcaatgtgtc atttccggct gctgtgtgtg agcggtggac gcgtgagaga    2570
gagagagaga gagagaatga gagagacggc gagctcgggc tcaattacct ccggcagata    2630
atctttctga cagccagcta gctgaggggg tacagagaga ggaccgattt actgaagaat    2690
tgcacagaga tgccgaatga atgtaaccta atagaaccct aatcaccccg ctgtgccctt    2750
cagcgaaaac tctcccttct ttgtgtgtat gttttgtttt gttttctttt tttcttgatg    2810
cactggacag tgacagccac actcagtacc cccacgtgtg gggtccatgg ctcttgaaat    2870 tgcttttttca cttttgatat agaagcaagt aaaaaaaaat gttttttaaa aattaataat    2930
aaataaataa aagaatatt ccaaaataaa aaaaaaaaa                           2970
```

<210> SEQ ID NO 2
<211> LENGTH: 402
<212> TYPE: PRT
<213> ORGANISM: Cow

<400> SEQUENCE: 2

```
Met Arg Met Ser Pro Val Phe Ala Cys Leu Ala Leu Gly Leu Ala Leu
 1               5                  10                  15

Ile Phe Gly Glu Gly Ser Ala Ser Tyr Gln Pro Gln Ser Ala Ala Ala
            20                  25                  30

Ser Leu Ala Thr Asp Phe Gly Val Lys Val Phe Gln Gln Val Val Arg
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Arg Gln Gln
65                  70                  75                  80

Ile Gln Glu Ala Met Gln Phe Lys Ile Glu Lys Gly Met Ala Pro
                85                  90                  95

Ala Phe His Arg Leu Tyr Lys Glu Leu Met Gly Pro Trp Asn Lys Asp
            100                 105                 110

Glu Ile Ser Thr Ala Asp Ala Ile Phe Val Gln Arg Asp Leu Glu Leu
        115                 120                 125

Val His Gly Phe Met Pro Asn Phe Phe Arg Leu Phe Arg Thr Thr Val
    130                 135                 140

Lys Gln Val Asp Phe Ser Glu Val Glu Arg Ala Arg Phe Ile Val Asn
145                 150                 155                 160

Asp Trp Val Lys Arg His Thr Lys Gly Met Ile Ser Asp Leu Leu Gly
                165                 170                 175

Glu Gly Ala Val Asp Gln Leu Thr Arg Leu Val Leu Val Asn Ala Leu
            180                 185                 190

Tyr Phe Asn Gly Gln Trp Lys Met Pro Phe Pro Glu Ser Asn Thr His
        195                 200                 205

His Arg Leu Phe His Lys Ser Asp Gly Ser Thr Ile Ser Val Pro Met
    210                 215                 220

Met Ala Gln Thr Asn Lys Phe Asn Tyr Thr Glu Phe Thr Thr Pro Asp
225                 230                 235                 240

Gly Arg Tyr Tyr Asp Ile Leu Glu Leu Pro Tyr His Gly Asn Thr Leu
                245                 250                 255

Ser Met Leu Ile Ala Ala Pro Tyr Glu Lys Glu Val Pro Leu Ser Ala
            260                 265                 270

Leu Thr Ser Ile Leu Asp Ala Glu Leu Ile Ser Gln Trp Lys Gly Asn
        275                 280                 285
```

-continued

```
Met Thr Arg Leu Thr Arg Leu Leu Val Leu Pro Lys Phe Ser Leu Glu
    290                 295                 300

Thr Glu Ile Asp Leu Arg Arg Pro Leu Glu Asn Leu Gly Met Thr Asp
305                 310                 315                 320

Met Phe Arg Pro Ser Gln Ala Asp Phe Ser Ser Phe Ser Asp Gln Glu
                325                 330                 335

Phe Leu Tyr Val Ser Gln Ala Leu Gln Lys Val Lys Ile Glu Val Asn
            340                 345                 350

Glu Ser Gly Thr Leu Ala Ser Ser Thr Ala Leu Val Val Ser Ala
        355                 360                 365

Arg Met Ala Pro Glu Glu Ile Ile Met Asp Arg Pro Phe Leu Phe Val
370                 375                 380

Val Arg His Asn Pro Thr Gly Thr Val Leu Phe Met Gly Gln Val Met
385                 390                 395                 400

Glu Pro
```

<210> SEQ ID NO 3
<211> LENGTH: 2876
<212> TYPE: DNA
<213> ORGANISM: Human
<220> FEATURE:
<221> NAME/KEY: CDS
<222> LOCATION: (76)..(1284)
<223> OTHER INFORMATION:

<400> SEQUENCE: 3

```
gaattcctgc agctcagcag ccgccgccag agcaggacga accgccaatc gcaaggcacc       60
tctgagaact tcagg atg cag atg tct cca gcc ctc acc tgc cta gtc ctg      111
               Met Gln Met Ser Pro Ala Leu Thr Cys Leu Val Leu
                 1               5                  10 ggc ctg gcc ctt gtc ttt ggt gaa ggg tct gct gtg cac cat ccc cca      159
Gly Leu Ala Leu Val Phe Gly Glu Gly Ser Ala Val His His Pro Pro
         15                  20                  25 tcc tac gtg gcc cac ctg gcc tca gac ttc ggg gtg agg gtg ttt cag      207
Ser Tyr Val Ala His Leu Ala Ser Asp Phe Gly Val Arg Val Phe Gln
 30                  35                  40 cag gtg gcg cag gcc tcc aag gac cgc aac gtg gtt ttc tca ccc tat      255
Gln Val Ala Gln Ala Ser Lys Asp Arg Asn Val Val Phe Ser Pro Tyr
45                  50                  55                  60 ggg gtg gcc tcg gtg ttg gcc atg ctc cag ctg aca aca gga gga gaa      303
Gly Val Ala Ser Val Leu Ala Met Leu Gln Leu Thr Thr Gly Gly Glu
                 65                  70                  75 acc cag cag cag att caa gca gct atg gga ttc aag att gat gac aag      351
Thr Gln Gln Gln Ile Gln Ala Ala Met Gly Phe Lys Ile Asp Asp Lys
             80                  85                  90 ggc atg gcc ccc gcc ctc cgg cat ctg tac aag gag ctc atg ggg cca      399
Gly Met Ala Pro Ala Leu Arg His Leu Tyr Lys Glu Leu Met Gly Pro
         95                 100                 105 tgg aac aag gat gag atc agc acc aca gac gcg atc ttc gtc cag cgg      447
Trp Asn Lys Asp Glu Ile Ser Thr Thr Asp Ala Ile Phe Val Gln Arg
     110                 115                 120 gat ctg aag ctg gtc cag ggc ttc atg ccc cac ttc ttc agg ctg ttc      495
Asp Leu Lys Leu Val Gln Gly Phe Met Pro His Phe Phe Arg Leu Phe
125                 130                 135                 140 cgg agc acg gtc aag caa gtg gac ttt tca gag gtg gag aga gcc aga      543
Arg Ser Thr Val Lys Gln Val Asp Phe Ser Glu Val Glu Arg Ala Arg
                145                 150                 155
```

```
ttc atc atc aat gac tgg gtg aag aca cac aca aaa ggt atg atc agc      591
Phe Ile Ile Asn Asp Trp Val Lys Thr His Thr Lys Gly Met Ile Ser
        160                 165                 170 aac ttg ctt ggg aaa gga gcc gtg gac cag ctg aca cgg ctg gtg ctg      639
Asn Leu Leu Gly Lys Gly Ala Val Asp Gln Leu Thr Arg Leu Val Leu
            175                 180                 185 gtg aat gcc ctc tac ttc aac ggc cag tgg aag act ccc ttc ccc gac      687
Val Asn Ala Leu Tyr Phe Asn Gly Gln Trp Lys Thr Pro Phe Pro Asp
        190                 195                 200 tcc agc acc cac cgc cgc ctc ttc cac aaa tca gac ggc agc act gtc      735
Ser Ser Thr His Arg Arg Leu Phe His Lys Ser Asp Gly Ser Thr Val
205                 210                 215                 220 tct gtg ccc atg atg gct cag acc aac aag ttc aac tat act gag ttc      783
Ser Val Pro Met Met Ala Gln Thr Asn Lys Phe Asn Tyr Thr Glu Phe
                225                 230                 235 acc acg ccc gat ggc cat tac tac gac atc ctg gaa ctg ccc tac cac      831
Thr Thr Pro Asp Gly His Tyr Tyr Asp Ile Leu Glu Leu Pro Tyr His
            240                 245                 250 ggg gac acc ctc agc atg ttc att gct gcc cct tat gaa aaa gag gtg      879
Gly Asp Thr Leu Ser Met Phe Ile Ala Ala Pro Tyr Glu Lys Glu Val
        255                 260                 265 cct ctc tct gcc ctc acc aac att ctg agt gcc cag ctc atc agc cac      927
Pro Leu Ser Ala Leu Thr Asn Ile Leu Ser Ala Gln Leu Ile Ser His
    270                 275                 280 tgg aaa ggc aac atg acc agg ctg ccc cgc ctc ctg gtt ctg ccc aag      975
Trp Lys Gly Asn Met Thr Arg Leu Pro Arg Leu Leu Val Leu Pro Lys
285                 290                 295                 300 ttc tcc ctg gag act gaa gtc gac ctc agg aag ccc cta gag aac ctg      1023
Phe Ser Leu Glu Thr Glu Val Asp Leu Arg Lys Pro Leu Glu Asn Leu
                305                 310                 315 gga atg acc gac atg ttc aga cag ttt cag gct gac ttc acg agt ctt      1071
Gly Met Thr Asp Met Phe Arg Gln Phe Gln Ala Asp Phe Thr Ser Leu
            320                 325                 330 tca gac caa gag cct ctc cac gtc gcg cag gcg ctg cag aaa gtg aag      1119
Ser Asp Gln Glu Pro Leu His Val Ala Gln Ala Leu Gln Lys Val Lys
        335                 340                 345 atc gag gtg aac gag agt ggc acg gtg gcc tcc tca tcc aca gct gtc      1167
Ile Glu Val Asn Glu Ser Gly Thr Val Ala Ser Ser Ser Thr Ala Val
    350                 355                 360 ata gtc tca gcc cgc atg gcc ccc gag gag atc atc atg gac aga ccc      1215
Ile Val Ser Ala Arg Met Ala Pro Glu Glu Ile Ile Met Asp Arg Pro
365                 370                 375                 380 ttc ctc ttt gtg gtc cgg cac aac ccc aca gga aca gtc ctt ttc atg      1263
Phe Leu Phe Val Val Arg His Asn Pro Thr Gly Thr Val Leu Phe Met
                385                 390                 395 ggc caa gtg atg gaa ccc tga ccctggggaa agacgccttc atctgggaca         1314
Gly Gln Val Met Glu Pro
                400 aaactggaga tgcatcggga agaagaaac tccgaagaaa agaattttag tgttaatgac     1374 tctttctgaa ggaagagaag acatttgcct tttgttaaaa gatggtaaac cagatctgtc    1434 tccaagacct tggcctctcc ttggaggacc tttaggtcaa actccctagt ctccacctga    1494 gaccctggga gagaagtttg aagcacaact cccttaaggt ctccaaacca gacggtgacg    1554 cctgcgggac catctgggc acctgcttcc accgtctct ctgccactc gggtctgcag       1614 acctggttcc cactgaggcc ctttgcagga tggaactacg gggcttacag gagcttttgt    1674 gtgcctggta gaaactattt ctgttccagt cacattgcca tcactcttgt actgcctgcc    1734 accgcggagg aggctggtga caggccaaag gccagtggaa gaaacaccct ttcatctcag    1794
```

-continued

```
agtccactgt ggcactggcc acccctcccc agtacagggg tgctgcaggt ggcagagtga   1854
atgtccccca tcatgtggcc caactctcct ggcctggcca tctccctccc cagaaacagt   1914
gtgcatgggt tattttggag tgtaggtgac ttgtttactc attgaagcag atttctgctt   1974
cctttatttt ttataggaat agaggaagaa atgtcagatg cgtgcccagc tcttcacccc   2034
ccaatctctt ggtggggagg ggtgtaccta aatatttatc atatccttgc ccttgagtgc   2094
ttgttagaga gaaagagaac tactaaggaa ataatatta tttaaactcg ctcctagtgt   2154
ttctttgtgg tctgtgtcac cgtatctcag gaagtccagc cacttgactg gcacacaccc   2214
ctccggacat ccagcgtgac ggagcccaca ctgccacctt gtggccgcct gagaccctcg   2274
cgcccccgc gcccccgcg cccctctttt tccccttgat ggaaattgac catacaattt   2334
catcctcctt cagggatca aaggacgga gtgggggac agagactcag atgaggacag   2394
agtggtttcc aatgtgttca atagatttag gagcagaaat gcaaggggct gcatgaccta   2454
ccaggacaga actttcccca attacagggt gactcacagc cgcattggtg actcacttca   2514
atgtgtcatt tccggctgct gtgtgtgagc agtggacacg tgaggggggg gtgggtgaga   2574
gagacaggca gctcggattc aactacctta gataatattt ctgaaaacct accagccaga   2634
gggtagggca caaagatgga tgtaatgcac tttgggaggc caaggcggga ggattgcttg   2694
agcccaggag ttcaagacca gcctgggcaa cataccaaga cccccgtctc tttaaaaata   2754
tatatatttt aaatatactt aaatatatat ttctaatatc tttaaatata tatatatatt   2814
ttaaagacca atttatggga gaattgcaca cagatgtgaa atgaatgtaa tctaatagaa   2874
gc                                                                  2876
```

```
<210> SEQ ID NO 4
<211> LENGTH: 402
<212> TYPE: PRT
<213> ORGANISM: Human

<400> SEQUENCE: 4
```

```
Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175
```

```
Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 5
<211> LENGTH: 1962
<212> TYPE: DNA
<213> ORGANISM: Human
<220> FEATURE:
<221> NAME/KEY: CDS
<222> LOCATION: (1)..(1161)
<223> OTHER INFORMATION:

<400> SEQUENCE: 5 gtc ttt ggt gaa ggg tct gct gtg cac cat ccc cca tcc tac gtg gcc      48
Val Phe Gly Glu Gly Ser Ala Val His His Pro Pro Ser Tyr Val Ala
1               5                   10                  15 cac ctg gcc tca gac ttc ggg gtg agg gtg ttt cag cag gtg gcg cag      96
His Leu Ala Ser Asp Phe Gly Val Arg Val Phe Gln Gln Val Ala Gln
            20                  25                  30 gcc tcc aag gac cgc aac gtg gtt ttc tca ccc tat ggg gtg gcc tcg     144
Ala Ser Lys Asp Arg Asn Val Val Phe Ser Pro Tyr Gly Val Ala Ser
        35                  40                  45 gtg ttg gcc atg ctc cag ctg aca aca gga gga gaa acc cag cag cag     192
Val Leu Ala Met Leu Gln Leu Thr Thr Gly Gly Glu Thr Gln Gln Gln
    50                  55                  60 att caa gca gct atg gga ttc aag att gat gac aag ggc atg gcc ccc     240
Ile Gln Ala Ala Met Gly Phe Lys Ile Asp Asp Lys Gly Met Ala Pro
65                  70                  75                  80 gcc ctc cgg cat ctg tac aag gag ctc atg ggg cca tgg aac aag gat     288
Ala Leu Arg His Leu Tyr Lys Glu Leu Met Gly Pro Trp Asn Lys Asp
                85                  90                  95
```

-continued

```
gag atc agc acc aca gac gcg atc ttc gtc cag cgg gat ctg aag ctg      336
Glu Ile Ser Thr Thr Asp Ala Ile Phe Val Gln Arg Asp Leu Lys Leu
        100                 105                 110 gtc cag ggc ttc atg ccc cac ttc ttc agg ctg ttc cgg agc acg gtc      384
Val Gln Gly Phe Met Pro His Phe Phe Arg Leu Phe Arg Ser Thr Val
    115                 120                 125 aag caa gtg gac ttt tca gag gtg gag aga gcc aga ttc atc atc aat      432
Lys Gln Val Asp Phe Ser Glu Val Glu Arg Ala Arg Phe Ile Ile Asn
130                 135                 140 gac tgg gtg aag aca cac aca aaa ggt atg atc agc aac ttg ctt ggg      480
Asp Trp Val Lys Thr His Thr Lys Gly Met Ile Ser Asn Leu Leu Gly
145                 150                 155                 160 aaa gga gcc gtg gac cag ctg aca cgg ctg gtg ctg gtg aat gcc ctc      528
Lys Gly Ala Val Asp Gln Leu Thr Arg Leu Val Leu Val Asn Ala Leu
                165                 170                 175 tac ttc aac ggc cag tgg aag act ccc ttc ccc gac tcc agc acc cac      576
Tyr Phe Asn Gly Gln Trp Lys Thr Pro Phe Pro Asp Ser Ser Thr His
            180                 185                 190 cgc cgc ctc ttc cac aaa tca gac ggc agc act gtc tct gtg ccc atg      624
Arg Arg Leu Phe His Lys Ser Asp Gly Ser Thr Val Ser Val Pro Met
        195                 200                 205 atg gct cag acc aac aag ttc aac tat act gag ttc acc acg ccc gat      672
Met Ala Gln Thr Asn Lys Phe Asn Tyr Thr Glu Phe Thr Thr Pro Asp
    210                 215                 220 ggc cat tac tac gac atc ctg gaa ctg ccc tac cac ggg gac acc ctc      720
Gly His Tyr Tyr Asp Ile Leu Glu Leu Pro Tyr His Gly Asp Thr Leu
225                 230                 235                 240 agc atg ttc att gct gcc cct tat gaa aaa gag gtg cct ctc tct gcc      768
Ser Met Phe Ile Ala Ala Pro Tyr Glu Lys Glu Val Pro Leu Ser Ala
                245                 250                 255 ctc acc aac att ctg agt gcc cag ctc atc agc cac tgg aaa ggc aac      816
Leu Thr Asn Ile Leu Ser Ala Gln Leu Ile Ser His Trp Lys Gly Asn
            260                 265                 270 atg acc agg ctg ccc cgc ctc ctg gtt ctg ccc aag ttc tcc ctg gag      864
Met Thr Arg Leu Pro Arg Leu Leu Val Leu Pro Lys Phe Ser Leu Glu
        275                 280                 285 act gaa gtc gac ctc agg aag ccc cta gag aac ctg gga atg acc gac      912
Thr Glu Val Asp Leu Arg Lys Pro Leu Glu Asn Leu Gly Met Thr Asp
    290                 295                 300 atg ttc aga cag ttt cag gct gac ttc acg agt ctt tca gac caa gag      960
Met Phe Arg Gln Phe Gln Ala Asp Phe Thr Ser Leu Ser Asp Gln Glu
305                 310                 315                 320 cct ctc cac gtc gcg cag gcg ctg cag aaa gtg aag atc gag gtg aac     1008
Pro Leu His Val Ala Gln Ala Leu Gln Lys Val Lys Ile Glu Val Asn
                325                 330                 335 gag agt ggc acg gtg gcc tcc tca tcc aca gct gtc ata gtc tca gcc     1056
Glu Ser Gly Thr Val Ala Ser Ser Ser Thr Ala Val Ile Val Ser Ala
            340                 345                 350 cgc atg gcc ccc gag gag atc atc atg gac aga ccc ttc ctc ttt gtg     1104
Arg Met Ala Pro Glu Glu Ile Ile Met Asp Arg Pro Phe Leu Phe Val
        355                 360                 365 gtc cgg cac aac ccc aca gga aca gtc ctt ttc atg ggc caa gtg atg     1152
Val Arg His Asn Pro Thr Gly Thr Val Leu Phe Met Gly Gln Val Met
    370                 375                 380 gaa ccc tga ccctgggaa agacgccttc atctgggaca aaactggaga              1201
Glu Pro
385
```

-continued

```
tgcatcggga aagaagaaac tccgaagaaa agaattttag tgttaatgac tctttctgaa   1261
ggaagagaag acatttgcct tttgttaaaa gatggtaaac cagatctgtc tccaagacct   1321
tggcctctcc ttggaggacc tttaggtcaa actccctagt ctccacctga gaccctggga   1381
gagaagtttg aagcacaact cccttaaggt ctccaaacca gacggtgacg cctgcgggac   1441
catctggggc acctgcttcc acccgtctct ctgcccactc gggtctgcag acctggttcc   1501
cactgaggcc ctttgcagga cggaactacg gggcttacag gagcttttgt gtgcctggta   1561
gaaactattt ctgttccagt cacattgcca tcactcttgt actgcctgcc accgcggagg   1621
aggctggtga caggccaaag gccagtggaa gaaacaccct ttcatctcag gtccactgt   1681 ggcactggcc acccctcccc agtacagggg tgctgcaggt ggcagagtga atgtccccca   1741
tcatgtggcc caactctcct ggcctggcca tctccctccc cagaaacagt gtgcatgggt   1801
tattttggag tgtaggtgac ttgtttactc attgaagcag atttctgctt cctttatttt   1861
ttataggaat agaggaagaa aggtcagatg cgtgcccagc tcttcacccc ccaatctctt   1921
ggtggggagg ggtgtaccta aatatttatc atatccttgc c                      1962
```

```
<210> SEQ ID NO 6
<211> LENGTH: 386
<212> TYPE: PRT
<213> ORGANISM: Human

<400> SEQUENCE: 6
```

| Val<br>1 | Phe | Gly | Glu | Gly<br>5 | Ser | Ala | Val | His | His<br>10 | Pro | Pro | Ser | Tyr | Val<br>15 | Ala |
|---|---|---|---|---|---|---|---|---|---|---|---|---|---|---|---|
| His | Leu | Ala | Ser<br>20 | Asp | Phe | Gly | Val | Arg<br>25 | Val | Phe | Gln | Gln | Val<br>30 | Ala | Gln |
| Ala | Ser | Lys<br>35 | Asp | Arg | Asn | Val | Val<br>40 | Phe | Ser | Pro | Tyr | Gly<br>45 | Val | Ala | Ser |
| Val<br>50 | Leu | Ala | Met | Leu | Gln<br>55 | Leu | Thr | Thr | Gly | Gly<br>60 | Glu | Thr | Gln | Gln |  |
| Ile<br>65 | Gln | Ala | Ala | Met | Gly<br>70 | Phe | Lys | Ile | Asp | Asp<br>75 | Lys | Gly | Met | Ala | Pro<br>80 |
| Ala | Leu | Arg | His | Leu<br>85 | Tyr | Lys | Glu | Leu | Met<br>90 | Gly | Pro | Trp | Asn | Lys<br>95 | Asp |
| Glu | Ile | Ser | Thr<br>100 | Thr | Asp | Ala | Ile | Phe<br>105 | Val | Gln | Arg | Asp | Leu<br>110 | Lys | Leu |
| Val | Gln | Gly<br>115 | Phe | Met | Pro | His | Phe<br>120 | Phe | Arg | Leu | Phe | Arg<br>125 | Ser | Thr | Val |
| Lys | Gln<br>130 | Val | Asp | Phe | Ser | Glu<br>135 | Val | Glu | Arg | Ala | Arg<br>140 | Phe | Ile | Ile | Asn |
| Asp<br>145 | Trp | Val | Lys | Thr | His<br>150 | Thr | Lys | Gly | Met | Ile<br>155 | Ser | Asn | Leu | Leu | Gly<br>160 |
| Lys | Gly | Ala | Val | Asp<br>165 | Gln | Leu | Thr | Arg | Leu<br>170 | Val | Leu | Val | Asn | Ala<br>175 | Leu |
| Tyr | Phe | Asn | Gly<br>180 | Gln | Trp | Lys | Thr | Pro<br>185 | Phe | Pro | Asp | Ser | Ser<br>190 | Thr | His |
| Arg | Arg | Leu<br>195 | Phe | His | Lys | Ser | Asp<br>200 | Gly | Ser | Thr | Val | Ser<br>205 | Val | Pro | Met |
| Met | Ala<br>210 | Gln | Thr | Asn | Lys | Phe<br>215 | Asn | Tyr | Thr | Glu | Phe<br>220 | Thr | Thr | Pro | Asp |
| Gly<br>225 | His | Tyr | Tyr | Asp | Ile<br>230 | Leu | Glu | Leu | Pro | Tyr<br>235 | His | Gly | Asp | Thr | Leu<br>240 |

-continued

```
Ser Met Phe Ile Ala Ala Pro Tyr Glu Lys Glu Val Pro Leu Ser Ala
            245                 250                 255

Leu Thr Asn Ile Leu Ser Ala Gln Leu Ile Ser His Trp Lys Gly Asn
        260                 265                 270

Met Thr Arg Leu Pro Arg Leu Leu Val Leu Pro Lys Phe Ser Leu Glu
    275                 280                 285

Thr Glu Val Asp Leu Arg Lys Pro Leu Glu Asn Leu Gly Met Thr Asp
290                 295                 300

Met Phe Arg Gln Phe Gln Ala Asp Phe Thr Ser Leu Ser Asp Gln Glu
305                 310                 315                 320

Pro Leu His Val Ala Gln Ala Leu Gln Lys Val Lys Ile Glu Val Asn
                325                 330                 335

Glu Ser Gly Thr Val Ala Ser Ser Thr Ala Val Ile Val Ser Ala
            340                 345                 350

Arg Met Ala Pro Glu Glu Ile Ile Met Asp Arg Pro Phe Leu Phe Val
        355                 360                 365

Val Arg His Asn Pro Thr Gly Thr Val Leu Phe Met Gly Gln Val Met
    370                 375                 380

Glu Pro
385

<210> SEQ ID NO 7
<211> LENGTH: 2970
<212> TYPE: DNA
<213> ORGANISM: Mink
<220> FEATURE:
<221> NAME/KEY: CDS
<222> LOCATION: (69)..(1271)
<223> OTHER INFORMATION:

<400> SEQUENCE: 7
tcgccaccgt cagcagcagc agcagcagga cagaccagca atcacaaggc acctttgaga      60 acttcagg atg cag atg tct aca gtc tgc ctt gcc ctg ggc ctg gcc ctt     110
         Met Gln Met Ser Thr Val Cys Leu Ala Leu Gly Leu Ala Leu
             1               5                   10 gtc ttt ggt gaa gca tcg gcc tcc tac ctc cac gag acc cgg gca gcg     158
Val Phe Gly Glu Ala Ser Ala Ser Tyr Leu His Glu Thr Arg Ala Ala
15              20                  25                  30 gaa ctg gcc aca gac ttc gga gtg aaa gtg ttt aag cag gtg gca cag     206
Glu Leu Ala Thr Asp Phe Gly Val Lys Val Phe Lys Gln Val Ala Gln
                35                  40                  45 gcc tcc aag gac cgc aac atg gtt ttt tcc ccc tat ggg ttg gcc tct     254
Ala Ser Lys Asp Arg Asn Met Val Phe Ser Pro Tyr Gly Leu Ala Ser
            50                  55                  60 gtc ctg gcc atg ttg cag ctg acc aca gca gga gag acc cgg cag cag     302
Val Leu Ala Met Leu Gln Leu Thr Thr Ala Gly Glu Thr Arg Gln Gln
        65                  70                  75 atc caa gag gcc atg cgg ttc cag att gat gag aag ggc atg gca cct     350
Ile Gln Glu Ala Met Arg Phe Gln Ile Asp Glu Lys Gly Met Ala Pro
    80                  85                  90 gcc ctc cgc caa ctg tac aag gaa ctc atg ggg ccg tgg aac aag gat     398
Ala Leu Arg Gln Leu Tyr Lys Glu Leu Met Gly Pro Trp Asn Lys Asp
95                  100                 105                 110 gag atc agt acc gcg gac gcc atc ttc gtc cag cgg gat ttg aag ctg     446
Glu Ile Ser Thr Ala Asp Ala Ile Phe Val Gln Arg Asp Leu Lys Leu
                115                 120                 125 gtc cac ggc ttc atg ccc tac ttc ttc agg ctg ttc caa acc aca gtc     494
Val His Gly Phe Met Pro Tyr Phe Phe Arg Leu Phe Gln Thr Thr Val
            130                 135                 140
```

| | | |
|---|---|---|
| aag cag gtg gac ttc tca gag gtg gag aga gcc agg ttc atc atc aac<br>Lys Gln Val Asp Phe Ser Glu Val Glu Arg Ala Arg Phe Ile Ile Asn<br>145 150 155 | 542 | |
| gac tgg gtg aag cga cac aca aaa ggc atg att ggc gac ctg ctg ggc<br>Asp Trp Val Lys Arg His Thr Lys Gly Met Ile Gly Asp Leu Leu Gly<br>160 165 170 | 590 | |
| aga ggg act gtg gac cag ctg acg cgt ctg atg ctg gtg aat gcc ctc<br>Arg Gly Thr Val Asp Gln Leu Thr Arg Leu Met Leu Val Asn Ala Leu<br>175 180 185 190 | 638 | |
| tac ttc aac ggc cag tgg aag acc cct ttc ccc aag tcg ggc acc cac<br>Tyr Phe Asn Gly Gln Trp Lys Thr Pro Phe Pro Lys Ser Gly Thr His<br>195 200 205 | 686 | |
| cac cgc ctc ttc cac aaa tct gat ggc agc acc gtc tcc gtg ccc atg<br>His Arg Leu Phe His Lys Ser Asp Gly Ser Thr Val Ser Val Pro Met<br>210 215 220 | 734 | |
| atg gct cag acc aac aag ttc aac tac acc gag ttt tct acc ccc gag<br>Met Ala Gln Thr Asn Lys Phe Asn Tyr Thr Glu Phe Ser Thr Pro Glu<br>225 230 235 | 782 | |
| ggc cgt tat tac gac atc ctg gaa ctg ccc tat cac gga gac acg ctc<br>Gly Arg Tyr Tyr Asp Ile Leu Glu Leu Pro Tyr His Gly Asp Thr Leu<br>240 245 250 | 830 | |
| agc atg ttc att gct gct ccc tat gaa aaa gac gtg cct ctt tct gcc<br>Ser Met Phe Ile Ala Ala Pro Tyr Glu Lys Asp Val Pro Leu Ser Ala<br>255 260 265 270 | 878 | |
| ctc acc aac atc ctg gat gcc cag ctc atc agc cag tgg aaa ggg aat<br>Leu Thr Asn Ile Leu Asp Ala Gln Leu Ile Ser Gln Trp Lys Gly Asn<br>275 280 285 | 926 | |
| atg acc aga cgg ctc cgc ctc ctg gtt ctg ccc aag ttc tcc ctg gag<br>Met Thr Arg Arg Leu Arg Leu Leu Val Leu Pro Lys Phe Ser Leu Glu<br>290 295 300 | 974 | |
| agc gaa gtc aac ctc cgg gga ccc ctg gag aac ttg ggg atg act gac<br>Ser Glu Val Asn Leu Arg Gly Pro Leu Glu Asn Leu Gly Met Thr Asp<br>305 310 315 | 1022 | |
| atg ttc agg cca aac cag gca gac ttc tcc agt ctt tca gat caa gag<br>Met Phe Arg Pro Asn Gln Ala Asp Phe Ser Ser Leu Ser Asp Gln Glu<br>320 325 330 | 1070 | |
| gca ctg tac gtg tcc cag gcg ctg cag aaa gtg aaa atc gag gtg aac<br>Ala Leu Tyr Val Ser Gln Ala Leu Gln Lys Val Lys Ile Glu Val Asn<br>335 340 345 350 | 1118 | |
| gag agc ggc acg gtg gcg tcc tcc tct aca gcc atc atc gtc tca gcc<br>Glu Ser Gly Thr Val Ala Ser Ser Ser Thr Ala Ile Ile Val Ser Ala<br>355 360 365 | 1166 | |
| cga atg gcc ccc gag gag atc atc atg gac aga ccc ttc ctc ttc gtg<br>Arg Met Ala Pro Glu Glu Ile Ile Met Asp Arg Pro Phe Leu Phe Val<br>370 375 380 | 1214 | |
| gtg cgg cac aac ccc aca gga acg gtc ctt ttc atg ggc caa gtg atg<br>Val Arg His Asn Pro Thr Gly Thr Val Leu Phe Met Gly Gln Val Met<br>385 390 395 | 1262 | |
| gaa ccc tga ccgcgagcac agcagccctc atctgggaca gaactggaga<br>Glu Pro<br>400 | 1311 | |
| tacatccaag aagaaggaac tctaaaggaa caaaatatat attttttcat taattttct | 1371 | |
| ggagaaaaag aagtcatttg ccctttaggg aaaaacaaaa caaaacaaaa accaaaaaaa | 1431 | |
| caaaaaaagg taaatctttc gaatctgcat cccagacctc agcctctccc aggaatggga | 1491 | |
| aagaggacct ttcagtaaaa ctccacggtg agcccccccg gagagacctc cgaagcacag | 1551 | |
| ctgggtctcc acaccagact gcaaacctca gacaaccact ggcgcagtgc tctgcccatc | 1611 | |
| cgggtctgca gacctggacc ccgccgagac cccggcagga tggcaccccca aggcttgcgg | 1671 |

-continued

```
gagcttttgt gtgcttggtg gaaacgattt gtgttccagg cacgtagctg tcactcctgc    1731
actgtctgcc actgctgagg aggctggcgg cgggccaaag aaggccagtg ggagaggcac    1791
cctttctgtt cgaggtctgt gccgccccga tcggacggtc tcgcggcccc gggcggagac    1851
ccgcccctga ctggccgtgg ccctccccag aaacagtgtg catatattat tttggagtgt    1911
aggtgacttg tttactcata ggagcaggtt tctgcttccc actaacttta ttttgcagga    1971
atggaggaat agaagtgaga tgcgtgcctg gttcttggct ctaatctccc ggtggggagg    2031
gtgggatgcc aggggtgtgc ttgggtattt aatcacatcc ttgtccttgt gtgcttgtga    2091
gagagaaaga ggactctcaa gaaaaacgta gtctatgtat ttgcttgtca tgttccctgg    2151
tggtttgtgt cttgcctctc aggagtctgg cccctgact agctgcccct ctgggcggca    2211
agcgtggtgg gacccacact gcccccttgt ggcttcctga gccccgtggt tcctctcccg    2271
tcctggccct tccactccat ggagaagacc cccgtcaaga tgatctaact ttagggacca    2331
aaaggatgtg gtgggtcaga gagattacag cgaggacagc atgctttcaa aattttccaa    2391
tatatttagg aacaggagag caaggggctg cacgacctaa caggacagaa ctttccccaa    2451
ttacagggtg attcacagcc gcattggtga ctcatttcga tgtgtcattt ccggctgctg    2511
tgtgcgagca gtggacacgt gagagagggg gagagagatt gagtgagaga gagaggagaa    2571
tgagagagac cacgagctcg gacttaacta ccctcgctag ataatctttc tgaaagccaa    2631
cgagctaggg ggcatggtat gaagacccag tttgttgaag aattgcacat agatgttgaa    2691
tgaatgaatg taacccaaac aggaccctaa ccgcctcccc cccaaacccc ccatccctc    2751
ttcagtgaaa aatctttgtt ctttgtttgt ttgtttctct taatgcactg gacagtgaca    2811
gctacacaca gtccccataa ggatacccaa gtgtggggtc caacattctt gaagttgtgt    2871
tgaatcatat gcttttcac ttttgatata taaacaagca aaatattttt taaaaataat    2931
aaataagtt aattaaaata taaaaaaaaa aaaaaaaa                             2970
```

<210> SEQ ID NO 8
<211> LENGTH: 400
<212> TYPE: PRT
<213> ORGANISM: Mink

<400> SEQUENCE: 8

```
Met Gln Met Ser Thr Val Cys Leu Ala Leu Gly Leu Ala Leu Val Phe
1               5                   10                  15

Gly Glu Ala Ser Ala Ser Tyr Leu His Glu Thr Arg Ala Ala Glu Leu
            20                  25                  30

Ala Thr Asp Phe Gly Val Lys Val Phe Lys Gln Val Ala Gln Ala Ser
        35                  40                  45

Lys Asp Arg Asn Met Val Phe Ser Pro Tyr Gly Leu Ala Ser Val Leu
    50                  55                  60

Ala Met Leu Gln Leu Thr Thr Ala Gly Glu Thr Arg Gln Gln Ile Gln
65                  70                  75                  80

Glu Ala Met Arg Phe Gln Ile Asp Glu Lys Gly Met Ala Pro Ala Leu
                85                  90                  95

Arg Gln Leu Tyr Lys Glu Leu Met Gly Pro Trp Asn Lys Asp Glu Ile
            100                 105                 110

Ser Thr Ala Asp Ala Ile Phe Val Gln Arg Asp Leu Lys Leu Val His
        115                 120                 125

Gly Phe Met Pro Tyr Phe Phe Arg Leu Phe Gln Thr Thr Val Lys Gln
    130                 135                 140
```

-continued

```
Val Asp Phe Ser Glu Val Glu Arg Ala Arg Phe Ile Ile Asn Asp Trp
145                 150                 155                 160

Val Lys Arg His Thr Lys Gly Met Ile Gly Asp Leu Leu Gly Arg Gly
                165                 170                 175

Thr Val Asp Gln Leu Thr Arg Leu Met Leu Val Asn Ala Leu Tyr Phe
            180                 185                 190

Asn Gly Gln Trp Lys Thr Pro Phe Pro Lys Ser Gly Thr His His Arg
        195                 200                 205

Leu Phe His Lys Ser Asp Gly Ser Thr Val Ser Val Pro Met Met Ala
    210                 215                 220

Gln Thr Asn Lys Phe Asn Tyr Thr Glu Phe Ser Thr Pro Glu Gly Arg
225                 230                 235                 240

Tyr Tyr Asp Ile Leu Glu Leu Pro Tyr His Gly Asp Thr Leu Ser Met
                245                 250                 255

Phe Ile Ala Ala Pro Tyr Glu Lys Asp Val Pro Leu Ser Ala Leu Thr
            260                 265                 270

Asn Ile Leu Asp Ala Gln Leu Ile Ser Gln Trp Lys Gly Asn Met Thr
        275                 280                 285

Arg Arg Leu Arg Leu Leu Val Leu Pro Lys Phe Ser Leu Glu Ser Glu
    290                 295                 300

Val Asn Leu Arg Gly Pro Leu Glu Asn Leu Gly Met Thr Asp Met Phe
305                 310                 315                 320

Arg Pro Asn Gln Ala Asp Phe Ser Ser Leu Ser Asp Gln Glu Ala Leu
                325                 330                 335

Tyr Val Ser Gln Ala Leu Gln Lys Val Lys Ile Glu Val Asn Glu Ser
            340                 345                 350

Gly Thr Val Ala Ser Ser Thr Ala Ile Ile Val Ser Ala Arg Met
        355                 360                 365

Ala Pro Glu Glu Ile Ile Met Asp Arg Pro Phe Leu Phe Val Val Arg
    370                 375                 380

His Asn Pro Thr Gly Thr Val Leu Phe Met Gly Gln Val Met Glu Pro
385                 390                 395                 400
```

<210> SEQ ID NO 9
<211> LENGTH: 2999
<212> TYPE: DNA
<213> ORGANISM: Mouse
<220> FEATURE:
<221> NAME/KEY: CDS
<222> LOCATION: (132)..(1340)
<223> OTHER INFORMATION:

<400> SEQUENCE: 9

```
tcaggctgca gcagagcccc gagagctttg tgaaggagga ccgccgcaca cccgcctccg      60
gcacacacag ccaaccacag ctgagcgaca gccaacaaga gccaatcaca aggcaccttt     120
gaatactcag g atg cag atg tct tca gcc ctt gct tgc ctc atc ctg ggc     170
            Met Gln Met Ser Ser Ala Leu Ala Cys Leu Ile Leu Gly
              1               5                  10 ctg gtt ctg gtc tct ggg aaa ggg ttc act tta ccc ctc cga gaa tcc     218
Leu Val Leu Val Ser Gly Lys Gly Phe Thr Leu Pro Leu Arg Glu Ser
         15                  20                  25 cac aca gcc cat cag gcc acc gac ttc gga gta aaa gtg ttt cag cag     266
His Thr Ala His Gln Ala Thr Asp Phe Gly Val Lys Val Phe Gln Gln
 30                  35                  40                  45 gtg gtc cag gcc tcc aaa gac cgg aat gtg gtc ttc tct ccc tat ggc     314
Val Val Gln Ala Ser Lys Asp Arg Asn Val Val Phe Ser Pro Tyr Gly
                 50                  55                  60
```

|     |     |
| --- | --- |
| gtg tcc tcg gtg ctg gct atg ctg cag atg acc aca gcg ggg aaa acc<br>Val Ser Ser Val Leu Ala Met Leu Gln Met Thr Thr Ala Gly Lys Thr<br>              65                            70                      75 | 362 |
| cgg cgg cag atc caa gat gct atg gga ttc aaa gtc aat gag aag ggc<br>Arg Arg Gln Ile Gln Asp Ala Met Gly Phe Lys Val Asn Glu Lys Gly<br>              80                            85                      90 | 410 |
| aca gct cat gcc ctc cgc cag ctc tcc aag gag ctc atg ggg ccg tgg<br>Thr Ala His Ala Leu Arg Gln Leu Ser Lys Glu Leu Met Gly Pro Trp<br> 95                            100                          105 | 458 |
| aac aag aat gag atc agt act gcg gat gcc atc ttt gtc cag cgg gac<br>Asn Lys Asn Glu Ile Ser Thr Ala Asp Ala Ile Phe Val Gln Arg Asp<br>110                         115                          120                      125 | 506 |
| cta gag ctg gtc cag ggc ttc atg ccc cac ttc ttc aag ctc ttc cag<br>Leu Glu Leu Val Gln Gly Phe Met Pro His Phe Phe Lys Leu Phe Gln<br>                    130                          135                      140 | 554 |
| act atg gtg aaa cag gtg gac ttc tca gag gtg gaa aga gcc aga ttt<br>Thr Met Val Lys Gln Val Asp Phe Ser Glu Val Glu Arg Ala Arg Phe<br>                  145                          150                      155 | 602 |
| atc atc aat gac tgg gtg gaa agg cat acc aaa ggt atg atc aat gac<br>Ile Ile Asn Asp Trp Val Glu Arg His Thr Lys Gly Met Ile Asn Asp<br>160                       165                          170 | 650 |
| tta ctg gcc aag ggg gct gta gac gag ctg aca cgc ctg gtg ctg gtg<br>Leu Leu Ala Lys Gly Ala Val Asp Glu Leu Thr Arg Leu Val Leu Val<br>     175                          180                      185 | 698 |
| aat gcc ctc tac ttc agt ggc caa tgg aag acc cct ttc tta gag gcc<br>Asn Ala Leu Tyr Phe Ser Gly Gln Trp Lys Thr Pro Phe Leu Glu Ala<br>190                       195                          200                      205 | 746 |
| agc acc cac cag cgc ctc ttc cac aag tct gat ggc agc acc gtc tct<br>Ser Thr His Gln Arg Leu Phe His Lys Ser Asp Gly Ser Thr Val Ser<br>                    210                          215                      220 | 794 |
| gtg ccc atg atg gct cag agc aac aag ttc aac tac act gag ttc acc<br>Val Pro Met Met Ala Gln Ser Asn Lys Phe Asn Tyr Thr Glu Phe Thr<br>                  225                          230                      235 | 842 |
| acc ccc gat ggg ctc gag tat gac gtc gtg gaa ctg ccc tac cag cgg<br>Thr Pro Asp Gly Leu Glu Tyr Asp Val Val Glu Leu Pro Tyr Gln Arg<br>                240                          245                      250 | 890 |
| gac acc ctc agc atg ttc atc gct gca ccc ttt gag aaa gat gtg cac<br>Asp Thr Leu Ser Met Phe Ile Ala Ala Pro Phe Glu Lys Asp Val His<br>     255                          260                      265 | 938 |
| ctc tcc gcc ctc acc aac atc ttg gat gct gaa ctc atc aga caa tgg<br>Leu Ser Ala Leu Thr Asn Ile Leu Asp Ala Glu Leu Ile Arg Gln Trp<br>270                       275                          280                      285 | 986 |
| aag ggc aac atg acc agg ctg ccc cgc ctc ctc atc ctg cct aag ttc<br>Lys Gly Asn Met Thr Arg Leu Pro Arg Leu Leu Ile Leu Pro Lys Phe<br>                  290                          295                      300 | 1034 |
| tct ctg gag act gaa gtg gac ctc aga ggg ccc ctg gag aag ttg ggc<br>Ser Leu Glu Thr Glu Val Asp Leu Arg Gly Pro Leu Glu Lys Leu Gly<br>                305                          310                      315 | 1082 |
| atg cct gac atg ttt agt gca acc ctg gcc gac ttc aca agt ctt tcc<br>Met Pro Asp Met Phe Ser Ala Thr Leu Ala Asp Phe Thr Ser Leu Ser<br>             320                          325                      330 | 1130 |
| gac caa gag cag ctc tct gta gca cag gca ctg caa aag gtc agg atc<br>Asp Gln Glu Gln Leu Ser Val Ala Gln Ala Leu Gln Lys Val Arg Ile<br>335                       340                          345 | 1178 |
| gag gta aac gag agc ggc aca gtg gcg tct tcc tcc aca gcc ttt gtc<br>Glu Val Asn Glu Ser Gly Thr Val Ala Ser Ser Ser Thr Ala Phe Val<br>350                       355                          360                      365 | 1226 |
| atc tca gcc cgc atg gcc ccc acg gag atg gtt ata gac cga tcc ttt<br>Ile Ser Ala Arg Met Ala Pro Thr Glu Met Val Ile Asp Arg Ser Phe<br>                  370                          375                      380 | 1274 |

|  |  |  |  |  |  |  |  |  |  |  |  |  |  | |
|---|---|---|---|---|---|---|---|---|---|---|---|---|---|---|
| ctc | ttt | gtg | gtt | cgg | cac | aac | ccg | aca | gag | aca | atc | ctc | ttc | atg ggg | 1322 |
| Leu | Phe | Val | Val | Arg | His | Asn | Pro | Thr | Glu | Thr | Ile | Leu | Phe | Met Gly |  |
|  |  | 385 |  |  |  |  | 390 |  |  |  |  | 395 |  |  |  |

| caa | gtg | atg | gag | cct | tga cagtgggaag agacgccttc atttggacga | 1370 |
|---|---|---|---|---|---|---|
| Gln | Val | Met | Glu | Pro |  |  |
|  |  |  | 400 |  |  |  |

```
aactggagat gttataagca gaaactctga agaaaaggtt atttaaagga ctctatgggg      1430
agaaagagaa ggcaactcct ccttaccccc cacactggta atctttccaa ccagcatccc      1490
agacctcgga ctcttgaagg gaaaagagtc taactccctc ctccctaggg attcctaccc      1550
cacaaaggtc tcatggacca tagaactcac agtacctgga tctgcccagc atgccctttg      1610
gacccagttc ccaccgaggc cccagcagag tggagggcac aacactttca ttcagcaaaa      1670
tcgtttgtgt tccagtcaca ctgtgggcac ctcttgcatc gcctgccatt gctgtggagg      1730
gtgccatggg ccaaaggaaa agcactgtc ctatctcaag gtccactgtg aaatgtcca        1790
ccttgcccac ctccaagggg caacggatag acagatcaaa tggtggccca atagcgagcc      1850
ttctccctgc tccctccctt gacacagctt gcttatgtta tttcagagtg taggtgactt      1910
gtttacacag ctttttcga cccacaaact tttttcattt ggaaagggtg taagaaaagt       1970
cggacgtgtg tgtgcctggc tcttcgtccc cagtctccca gtgggggggc cctggggaga      2030
ttccaggggt gtgattgaat atttatctct tgctcttgta tgtttgttgg ggagaagaag      2090
cactttaag gaaaatgctt cttatttaaa ccgtggcata cggcatccca tttggggtct       2150
gcatccctgt atgtcagggg tgcatcactc cacaaacctg cccctctggg tagcctcgtg      2210
atggggctca cactgccgcc tagtggcagc cgaacacacc cttacccggt ccctccctcc      2270
ctcccccccc ccccccccc ccgtggctct ttttccttag ggaccttgcc aaggtgatgc       2330
ttggcaaccc acgttaaagg aagggggaa aaaagattag atggaagaga gagagatttg       2390
agagagggca aagtggtttc aaatttttcc aaggcatcca gaagcagaga gggaaagggg      2450
gctgtgtgac ctaacaggac agaactttct ccaattactg ggtgagtcag agctgcactg      2510
gtgactcact tcaatgtgtc atttccggct gctgtatgtg agcagtggac acgtgggggg      2570
gcggggggg gatgaaagag acagcagctc ctggtcaacc accttagtta gataatcttt       2630
tttgaaagct tcctagctgg aggtatgatc agaaaaccaa tttactgaaa aactgcacaa      2690
gaaggtaccg tgaatgaatt cctagcagg ccactctgca tctgttatgt ctccaccgga       2750
aaaaaaataa tcatgttggt gtttttgctt ttctctctct ccctctttct ctctgatttt      2810
tttttcctct cttttcatta tgcactggac agccacacac cgtgtaccat agggccccaa      2870
atgtggggtc acatggtctt gaattttgtt ggttacatat gccttttgt tgttgtttgt       2930
cttcactttt gatatataaa caggtaaata tgttttttaa aaaatactaa atatagagaa      2990
tatgcaaac                                                             2999
```

<210> SEQ ID NO 10
<211> LENGTH: 402
<212> TYPE: PRT
<213> ORGANISM: Mouse

<400> SEQUENCE: 10

| Met | Gln | Met | Ser | Ser | Ala | Leu | Ala | Cys | Leu | Ile | Leu | Gly | Leu | Val | Leu |
|---|---|---|---|---|---|---|---|---|---|---|---|---|---|---|---|
| 1 |  |  |  | 5 |  |  |  |  | 10 |  |  |  |  | 15 |  |

| Val | Ser | Gly | Lys | Gly | Phe | Thr | Leu | Pro | Leu | Arg | Glu | Ser | His | Thr | Ala |
|---|---|---|---|---|---|---|---|---|---|---|---|---|---|---|---|
|  |  |  | 20 |  |  |  |  | 25 |  |  |  |  | 30 |  |  |

```
His Gln Ala Thr Asp Phe Gly Val Lys Val Phe Gln Val Val Gln
        35                  40                  45

Ala Ser Lys Asp Arg Asn Val Val Phe Ser Pro Tyr Gly Val Ser Ser
    50                  55                  60

Val Leu Ala Met Leu Gln Met Thr Thr Ala Gly Lys Thr Arg Arg Gln
65                  70                  75                  80

Ile Gln Asp Ala Met Gly Phe Lys Val Asn Glu Lys Gly Thr Ala His
                85                  90                  95

Ala Leu Arg Gln Leu Ser Lys Glu Leu Met Gly Pro Trp Asn Lys Asn
            100                 105                 110

Glu Ile Ser Thr Ala Asp Ala Ile Phe Val Gln Arg Asp Leu Glu Leu
        115                 120                 125

Val Gln Gly Phe Met Pro His Phe Phe Lys Leu Phe Gln Thr Met Val
    130                 135                 140

Lys Gln Val Asp Phe Ser Glu Val Glu Arg Ala Arg Phe Ile Ile Asn
145                 150                 155                 160

Asp Trp Val Glu Arg His Thr Lys Gly Met Ile Asn Asp Leu Leu Ala
                165                 170                 175

Lys Gly Ala Val Asp Glu Leu Thr Arg Leu Val Leu Val Asn Ala Leu
            180                 185                 190

Tyr Phe Ser Gly Gln Trp Lys Thr Pro Phe Leu Glu Ala Ser Thr His
        195                 200                 205

Gln Arg Leu Phe His Lys Ser Asp Gly Ser Thr Val Ser Val Pro Met
    210                 215                 220

Met Ala Gln Ser Asn Lys Phe Asn Tyr Thr Glu Phe Thr Thr Pro Asp
225                 230                 235                 240

Gly Leu Glu Tyr Asp Val Val Glu Leu Pro Tyr Gln Arg Asp Thr Leu
                245                 250                 255

Ser Met Phe Ile Ala Ala Pro Phe Glu Lys Asp Val His Leu Ser Ala
            260                 265                 270

Leu Thr Asn Ile Leu Asp Ala Glu Leu Ile Arg Gln Trp Lys Gly Asn
        275                 280                 285

Met Thr Arg Leu Pro Arg Leu Leu Ile Leu Pro Lys Phe Ser Leu Glu
    290                 295                 300

Thr Glu Val Asp Leu Arg Gly Pro Leu Glu Lys Leu Gly Met Pro Asp
305                 310                 315                 320

Met Phe Ser Ala Thr Leu Ala Asp Phe Thr Ser Leu Ser Asp Gln Glu
                325                 330                 335

Gln Leu Ser Val Ala Gln Ala Leu Gln Lys Val Arg Ile Glu Val Asn
            340                 345                 350

Glu Ser Gly Thr Val Ala Ser Ser Thr Ala Phe Val Ile Ser Ala
        355                 360                 365

Arg Met Ala Pro Thr Glu Met Val Ile Asp Arg Ser Phe Leu Phe Val
    370                 375                 380

Val Arg His Asn Pro Thr Glu Thr Ile Leu Phe Met Gly Gln Val Met
385                 390                 395                 400

Glu Pro

<210> SEQ ID NO 11
<211> LENGTH: 2999
<212> TYPE: DNA
<213> ORGANISM: Mouse
```

```
-continued

<220> FEATURE:
<221> NAME/KEY: CDS
<222> LOCATION: (132)..(1340)
<223> OTHER INFORMATION:

<400> SEQUENCE: 11
tcaggctgca gcagagcccc gagagctttg tgaaggagga ccgccgcaca cccgcctccg      60
gcacacacag ccaaccacag ctgagcgaca gccaacaaga gccaatcaca aggcaccttt     120
gaatactcag g atg cag atg tct tca gcc ctt gct tgc ctc atc ctg ggc      170
            Met Gln Met Ser Ser Ala Leu Ala Cys Leu Ile Leu Gly
              1               5                  10 ctg gtt ctg gtc tct ggg aaa ggg ttc act tta ccc ctc cga gaa tcc       218
Leu Val Leu Val Ser Gly Lys Gly Phe Thr Leu Pro Leu Arg Glu Ser
     15                  20                  25 cac aca gcc cat cag gcc acc gac ttc gga gta aaa gtg ttt cag cag       266
His Thr Ala His Gln Ala Thr Asp Phe Gly Val Lys Val Phe Gln Gln
 30                  35                  40                  45 gtc gtc cag gcc tcc aaa gac cgg aat gtg gtc ttc tct ccc tat ggc       314
Val Val Gln Ala Ser Lys Asp Arg Asn Val Val Phe Ser Pro Tyr Gly
                 50                  55                  60 gtg tcc tcg gtg ctg gct atg ctg cag atg acc aca gcg ggg aaa acc       362
Val Ser Ser Val Leu Ala Met Leu Gln Met Thr Thr Ala Gly Lys Thr
             65                  70                  75 cgg cgg cag atc caa gat gct atg gga ttc aaa gtc aat gag aag ggc       410
Arg Arg Gln Ile Gln Asp Ala Met Gly Phe Lys Val Asn Glu Lys Gly
         80                  85                  90 aca gct cat gcc ctc cgc cag ctc tcc aag gag ctc atg ggg ccg tgg       458
Thr Ala His Ala Leu Arg Gln Leu Ser Lys Glu Leu Met Gly Pro Trp
     95                 100                 105 aac aag aat gag atc agt act gcg gat gcc atc ttt gtc cag cgg gac       506
Asn Lys Asn Glu Ile Ser Thr Ala Asp Ala Ile Phe Val Gln Arg Asp
110                 115                 120                 125 cta gag ctg gtc cag ggc ttc atg ccc cac ttc ttc aag ctc ttc cag       554
Leu Glu Leu Val Gln Gly Phe Met Pro His Phe Phe Lys Leu Phe Gln
                130                 135                 140 act atg gtg aaa cag gtg gac ttc tca gag gtg gaa aga gcc aga ttt       602
Thr Met Val Lys Gln Val Asp Phe Ser Glu Val Glu Arg Ala Arg Phe
            145                 150                 155 atc atc aat gac tgg gtg gaa agg cat acc aaa ggt atg atc aat gac       650
Ile Ile Asn Asp Trp Val Glu Arg His Thr Lys Gly Met Ile Asn Asp
        160                 165                 170 tta ctg gcc aag ggg gct gta gac gag ctg aca cgc ctg gtg ctg gtg       698
Leu Leu Ala Lys Gly Ala Val Asp Glu Leu Thr Arg Leu Val Leu Val
    175                 180                 185 aat gcc ctc tac ttc agt ggc caa tgg aag acc cct ttc tta gag gcc       746
Asn Ala Leu Tyr Phe Ser Gly Gln Trp Lys Thr Pro Phe Leu Glu Ala
190                 195                 200                 205 agc acc cac cag cgc ctc ttc cac aag tct gat ggc agc acc gtc tct       794
Ser Thr His Gln Arg Leu Phe His Lys Ser Asp Gly Ser Thr Val Ser
                210                 215                 220 gtg ccc atg atg gct cag agc aac aag ttc aac tac act gag ttc acc       842
Val Pro Met Met Ala Gln Ser Asn Lys Phe Asn Tyr Thr Glu Phe Thr
            225                 230                 235 acc ccc gat ggg ctc gag tat gac gtc gtg gaa ctg ccc tac cag cgg       890
Thr Pro Asp Gly Leu Glu Tyr Asp Val Val Glu Leu Pro Tyr Gln Arg
        240                 245                 250 gac acc ctc agc atg ttc atc gct gca ccc ttt gag aaa gat gtg cac       938
Asp Thr Leu Ser Met Phe Ile Ala Ala Pro Phe Glu Lys Asp Val His
    255                 260                 265
```

-continued

| | | |
|---|---|---|
| ctc tcc gcc ctc acc aac atc ttg gat gct gaa ctc atc aga caa tgg<br>Leu Ser Ala Leu Thr Asn Ile Leu Asp Ala Glu Leu Ile Arg Gln Trp<br>270                      275                    280                    285 | 986 |
| aag ggc aac atg acc agg ctg ccc cgc ctc ctc atc ctg cct aag ttc<br>Lys Gly Asn Met Thr Arg Leu Pro Arg Leu Leu Ile Leu Pro Lys Phe<br>                    290                    295                    300 | 1034 |
| tct ctg gag act gaa gtg gac ctc aga ggg ccc ctg gag aag ttg ggc<br>Ser Leu Glu Thr Glu Val Asp Leu Arg Gly Pro Leu Glu Lys Leu Gly<br>              305                    310                    315 | 1082 |
| atg cct gac atg ttt agt gca acc ctg gcc gac ttc aca agt ctt tcc<br>Met Pro Asp Met Phe Ser Ala Thr Leu Ala Asp Phe Thr Ser Leu Ser<br>320                      325                    330 | 1130 |
| gac caa gag cag ctc tct gta gca cag gca ctg caa aag gtc agg atc<br>Asp Gln Glu Gln Leu Ser Val Ala Gln Ala Leu Gln Lys Val Arg Ile<br>     335                    340                    345 | 1178 |
| gag gta aac gag agc ggc aca gtg gcg tct tcc tcc aca gcc ttt gtc<br>Glu Val Asn Glu Ser Gly Thr Val Ala Ser Ser Ser Thr Ala Phe Val<br>350                      355                    360                    365 | 1226 |
| atc tca gcc cgc atg gcc ccc acg gag atg gtt ata gac cga tcc ttt<br>Ile Ser Ala Arg Met Ala Pro Thr Glu Met Val Ile Asp Arg Ser Phe<br>                    370                    375                    380 | 1274 |
| ctc ttt gtg gtt cgg cac aac ccg aca gag aca atc ctc ttc atg ggg<br>Leu Phe Val Val Arg His Asn Pro Thr Glu Thr Ile Leu Phe Met Gly<br>     385                    390                    395 | 1322 |
| caa gtg atg gag cct tga cagtgggaag agacgccttc atttggacga<br>Gln Val Met Glu Pro<br>           400 | 1370 |
| aactggagat gttataagca gaaactctga agaaaaggtt atttaaagga ctctatgggg | 1430 |
| agaaagagaa ggcaactcct ccttaccccc cacactggta atctttccaa ccagcatccc | 1490 |
| agacctcgga ctcttgaagg gaaaagagtc taactccctc ctccctaggg attcctaccc | 1550 |
| cacaaaggtc tcatggacca tagaactcac agtacctgga tctgcccagc atgcccttg | 1610 |
| gacccagttc ccaccgaggc cccagcagag tggagggcac aacactttca ttcagcaaaa | 1670 |
| tcgtttgtgt tccagtcaca ctgtgggcac ctcttgcatc gcctgccatt gctgtggagg | 1730 |
| gtgccatggg ccaaaggaaa aagcactgtc ctatctcaag gtccactgtg gaaatgtcca | 1790 |
| ccttgcccac ctccaagggg caacggatag acagatcaaa tggtggccca atagcgagcc | 1850 |
| ttctccctgc tccctcccct gacacagctt gcttatgtta tttcagagtg taggtgactt | 1910 |
| gtttacacag ctttttttcga cccacaaact ttttcattt ggaaagggtg taagaaaagt | 1970 |
| cggacgtgtg tgtgcctggc tcttcgtccc cagtctccca gtggggggc cctggggaga | 2030 |
| ttccagggt gtgattgaat atttatctct tgctcttgta tgtttgttgg ggagaagaag | 2090 |
| cacttttaag gaaaatgctt cttatttaaa ccgtggcata cggcatccca tttgggtct | 2150 |
| gcatccctgt atgtcagggg tgcatcactc cacaaacctg ccctctggg tagcctcgtg | 2210 |
| atggggctca cactgccgcc tagtggcagc cgaacacacc cttacccggt ccctccctcc | 2270 |
| ctcccccccc cccccccccc ccgtggctct ttttccttag ggaccttgcc aaggtgatgc | 2330 |
| ttggcaaccc acgttaaagg aaggggggaa aaagattag atggaagaga gagagatttg | 2390 |
| agagagggca aagtggtttc aaattttttcc aaggcatcca gaagcagaga gggaaaaggg | 2450 |
| gctgtgtgac ctaacaggac agaactttct ccaattactg ggtgagtcag agctgcactg | 2510 |
| gtgactcact tcaatgtgtc atttccggct gctgtatgtg agcagtggac acgtgggggg | 2570 |
| gcgggggggg gatgaaagag acagcagctc ctggtcaacc accttagtta gataatcttt | 2630 |
| tttgaaagct tcctagctgg aggtatgatc agaaaaccaa tttactgaaa aactgcacaa | 2690 |

```
gaaggtaccg tgaatgaatt tcctagcagg ccactctgca tctgttatgt ctccaccgga    2750
aaaaaaataa tcatgttggt gtttttgctt ttctctctct ccctctttct ctctgatttt    2810
tttttcctct cttttcatta tgcactggac agccacacac cgtgtaccat agggccccaa    2870
atgtggggtc acatggtctt gaattttgtt ggttacatat gccttttttgt tgttgtttgt    2930 cttcactttt gatatataaa caggtaaata tgttttttaa aaaatactaa atatagagaa    2990
tatgcaaac                                                            2999
```

<210> SEQ ID NO 12
<211> LENGTH: 402
<212> TYPE: PRT
<213> ORGANISM: Mouse

<400> SEQUENCE: 12

```
Met Gln Met Ser Ser Ala Leu Ala Cys Leu Ile Leu Gly Leu Val Leu
1               5                   10                  15

Val Ser Gly Lys Gly Phe Thr Leu Pro Leu Arg Glu Ser His Thr Ala
            20                  25                  30

His Gln Ala Thr Asp Phe Gly Val Lys Val Phe Gln Gln Val Val Gln
        35                  40                  45

Ala Ser Lys Asp Arg Asn Val Val Phe Ser Pro Tyr Gly Val Ser Ser
    50                  55                  60

Val Leu Ala Met Leu Gln Met Thr Thr Ala Gly Lys Thr Arg Arg Gln
65                  70                  75                  80

Ile Gln Asp Ala Met Gly Phe Lys Val Asn Glu Lys Gly Thr Ala His
                85                  90                  95

Ala Leu Arg Gln Leu Ser Lys Glu Leu Met Gly Pro Trp Asn Lys Asn
            100                 105                 110

Glu Ile Ser Thr Ala Asp Ala Ile Phe Val Gln Arg Asp Leu Glu Leu
        115                 120                 125

Val Gln Gly Phe Met Pro His Phe Phe Lys Leu Phe Gln Thr Met Val
    130                 135                 140

Lys Gln Val Asp Phe Ser Glu Val Glu Arg Ala Arg Phe Ile Ile Asn
145                 150                 155                 160

Asp Trp Val Glu Arg His Thr Lys Gly Met Ile Asn Asp Leu Leu Ala
                165                 170                 175

Lys Gly Ala Val Asp Glu Leu Thr Arg Leu Val Leu Val Asn Ala Leu
            180                 185                 190

Tyr Phe Ser Gly Gln Trp Lys Thr Pro Phe Leu Glu Ala Ser Thr His
        195                 200                 205

Gln Arg Leu Phe His Lys Ser Asp Gly Ser Thr Val Ser Val Pro Met
    210                 215                 220

Met Ala Gln Ser Asn Lys Phe Asn Tyr Thr Glu Phe Thr Thr Pro Asp
225                 230                 235                 240

Gly Leu Glu Tyr Asp Val Val Glu Leu Pro Tyr Gln Arg Asp Thr Leu
                245                 250                 255

Ser Met Phe Ile Ala Ala Pro Phe Glu Lys Asp Val His Leu Ser Ala
            260                 265                 270

Leu Thr Asn Ile Leu Asp Ala Glu Leu Ile Arg Gln Trp Lys Gly Asn
        275                 280                 285

Met Thr Arg Leu Pro Arg Leu Leu Ile Leu Pro Lys Phe Ser Leu Glu
    290                 295                 300

Thr Glu Val Asp Leu Arg Gly Pro Leu Glu Lys Leu Gly Met Pro Asp
305                 310                 315                 320
```

```
Met Phe Ser Ala Thr Leu Ala Asp Phe Thr Ser Leu Ser Asp Gln Glu
            325                 330                 335

Gln Leu Ser Val Ala Gln Ala Leu Gln Lys Val Arg Ile Glu Val Asn
        340                 345                 350

Glu Ser Gly Thr Val Ala Ser Ser Thr Ala Phe Val Ile Ser Ala
            355                 360                 365

Arg Met Ala Pro Thr Glu Met Val Ile Asp Arg Ser Phe Leu Phe Val
    370                 375                 380

Val Arg His Asn Pro Thr Glu Thr Ile Leu Phe Met Gly Gln Val Met
385                 390                 395                 400

Glu Pro

<210> SEQ ID NO 13
<211> LENGTH: 3053
<212> TYPE: DNA
<213> ORGANISM: Rat
<220> FEATURE:
<221> NAME/KEY: CDS
<222> LOCATION: (119)..(1327)
<223> OTHER INFORMATION:

<400> SEQUENCE: 13
cccccgagag ctttgtgaag gaggaacgct gcacacccgc ctcccgcagc acacagccaa      60
ccacagctga gcgacacgca acaagagcca atcacaaggc acttccgaaa gctccagg     118
```

| | | | | | | | | | | | | | | | | |
|---|---|---|---|---|---|---|---|---|---|---|---|---|---|---|---|---|
| atg | cag | atg | tct | tca | gcc | ctc | act | tgc | ctc | acc | ctg | ggc | ctg | gtt | ctg | 166 |
| Met | Gln | Met | Ser | Ser | Ala | Leu | Thr | Cys | Leu | Thr | Leu | Gly | Leu | Val | Leu | |
| 1 | | | | 5 | | | | | 10 | | | | | 15 | | |

```
gtc ttt ggg aaa ggg ttc gct tca ccc ctt cca gag tcc cat aca gcc      214
Val Phe Gly Lys Gly Phe Ala Ser Pro Leu Pro Glu Ser His Thr Ala
             20                  25                  30 cag cag gcc acc aac ttc gga gta aaa gtg ttt cag cat gtg gtc cag      262
Gln Gln Ala Thr Asn Phe Gly Val Lys Val Phe Gln His Val Val Gln
         35                  40                  45 gcc tcc aaa gac cga aat gtg gtc ttc tct ccc tac ggc gtg tcc tcg      310
Ala Ser Lys Asp Arg Asn Val Val Phe Ser Pro Tyr Gly Val Ser Ser
     50                  55                  60 gtg ctg gct atg ctg cag ctg acc aca gca ggg aaa acc cgg cag cag      358
Val Leu Ala Met Leu Gln Leu Thr Thr Ala Gly Lys Thr Arg Gln Gln
 65                  70                  75                  80 atc caa gat gct atg gga ttc aat atc agt gag agg ggc aca gct cct      406
Ile Gln Asp Ala Met Gly Phe Asn Ile Ser Glu Arg Gly Thr Ala Pro
                 85                  90                  95 gcc ctc cga aag ctc tcc aag gag ctc atg ggg tca tgg aac aag aat      454
Ala Leu Arg Lys Leu Ser Lys Glu Leu Met Gly Ser Trp Asn Lys Asn
            100                 105                 110 gag atc agt act gcg gac gcc atc ttt gtc cag cgg gac cta gag ctg      502
Glu Ile Ser Thr Ala Asp Ala Ile Phe Val Gln Arg Asp Leu Glu Leu
        115                 120                 125 gtc cag ggc ttc atg ccc cac ttc ttc aag ctc ttc cgg acc acg gtg      550
Val Gln Gly Phe Met Pro His Phe Phe Lys Leu Phe Arg Thr Thr Val
    130                 135                 140 aag cag gtg gac ttc tca gag gtg gaa aga gcc aga ttc atc atc aac      598
Lys Gln Val Asp Phe Ser Glu Val Glu Arg Ala Arg Phe Ile Ile Asn
145                 150                 155                 160 gac tgg gtg gag agg cac acc aaa ggt atg atc agt gac tta ctg gcc      646
Asp Trp Val Glu Arg His Thr Lys Gly Met Ile Ser Asp Leu Leu Ala
                165                 170                 175
```

```
aag ggg gct gta aat gag ctg aca cgc ctg gtg ctg gtg aac gcc ctc         694
Lys Gly Ala Val Asn Glu Leu Thr Arg Leu Val Leu Val Asn Ala Leu
            180                 185                 190 tat ttc aac ggc caa tgg aag acc ccc ttc tta gag gcc agc acc cac         742
Tyr Phe Asn Gly Gln Trp Lys Thr Pro Phe Leu Glu Ala Ser Thr His
        195                 200                 205 cag cgc ctg ttc cac aag tct gat ggt agc acc atc tcc gtg ccc atg         790
Gln Arg Leu Phe His Lys Ser Asp Gly Ser Thr Ile Ser Val Pro Met
    210                 215                 220 atg gct cag aac aac aag ttc aac tac act gag ttc acc act ccg gat         838
Met Ala Gln Asn Asn Lys Phe Asn Tyr Thr Glu Phe Thr Thr Pro Asp
225                 230                 235                 240 ggg cac gag tac gac atc ctg gaa ctg ccc tac cac ggc gaa acc ctc         886
Gly His Glu Tyr Asp Ile Leu Glu Leu Pro Tyr His Gly Glu Thr Leu
                245                 250                 255 agc atg ttc att gca gca ccc ttt gaa aaa gat gtg ccc ctc tcc gcc         934
Ser Met Phe Ile Ala Ala Pro Phe Glu Lys Asp Val Pro Leu Ser Ala
            260                 265                 270 atc acc aac att ttg gac gct gag ctc atc aga caa tgg aag agc aac         982
Ile Thr Asn Ile Leu Asp Ala Glu Leu Ile Arg Gln Trp Lys Ser Asn
        275                 280                 285 atg acc agg ctg ccc cgc ctc ctc atc ctg cct aag ttc tct ctg gag        1030
Met Thr Arg Leu Pro Arg Leu Leu Ile Leu Pro Lys Phe Ser Leu Glu
    290                 295                 300 act gaa gtg gac ctc aga ggg ccc ctg gag aag ctg ggc atg act gac        1078
Thr Glu Val Asp Leu Arg Gly Pro Leu Glu Lys Leu Gly Met Thr Asp
305                 310                 315                 320 atc ttc agc tca acc cag gcc gac ttc aca agt ctt tcc gac caa gag        1126
Ile Phe Ser Ser Thr Gln Ala Asp Phe Thr Ser Leu Ser Asp Gln Glu
                325                 330                 335 cag ctc tct gta gca caa gca cta caa aag gtc aag atc gag gtg aac        1174
Gln Leu Ser Val Ala Gln Ala Leu Gln Lys Val Lys Ile Glu Val Asn
            340                 345                 350 gag agc ggc aca gtg gcg tct tcc tcc aca gcc att cta gtc tca gcc        1222
Glu Ser Gly Thr Val Ala Ser Ser Ser Thr Ala Ile Leu Val Ser Ala
        355                 360                 365 cgc atg gcc ccc acg gag atg gtt tta gac cga tcc ttt ctc ttt gtg        1270
Arg Met Ala Pro Thr Glu Met Val Leu Asp Arg Ser Phe Leu Phe Val
    370                 375                 380 gtt cgg cac aat cca aca gag aca atc ctc ttc atg ggc cag ctg atg        1318
Val Arg His Asn Pro Thr Glu Thr Ile Leu Phe Met Gly Gln Leu Met
385                 390                 395                 400 gag cct tga gagtgggatg agaagccttt cctttgggac aaaactggac               1367
Glu Pro gtgttataag cagagactct gaagaaaaga attgttttaa ggactctttg gggagaaaga      1427
gaaggccttt ctttcttacc ccggcactgg taaatctttc caaccagcct cccagacctc      1487
agactctcga agaggaaaga gtctaactcc ctcactaggg acctatctta ctaaggtctc      1547
atccaaccat agaactcaca gaatctggat ctgcccagca ttcagccttt ggacccagtt      1607
cccaccaagg ccccagcagg gccaacccac tacgccttca ctcagcaaag tcttttgtgt      1667
tccagtcaca ctctgggtac ctcttgtatc gtcctccatt gctatgaagg atgacccagg      1727
ccaaaggaag aagcactgtc ctatctcaag gtccactgtg gaaatgaaca ccttgcccat      1787
ccccaagggg cagcagatag acagatcgaa tgatcgcccg atatcaagcc ttctcccagc      1847
tcccgtcctg ccctcccttc cctgacagcc gccttgtgtt atttcagagt gtagatgact      1907
tgtttacagc ttttttcgac ccacaaactt ttctcatttt gaaagcgtga agaaaggtc       1967
```

-continued

```
agatgtgcac gtgccttgct ctttatcctg ggtctccctg tgaggggaga ggggtcctgg      2027
ggagattcca ggggtgtgat tgaatattta tcttgtttat cttatacgtt tgttggggag      2087
aagaagcact attaaggaga aagccttttta tttaaaccat ggcatatggt gtcccatttg     2147
gggtctgtat ccctgtatgt cagggaggca tcactccaca aacccgcccc tcgggtggcc      2207
cggcgtcggg gctcacactg ccgcctagtg gcagccgaac acgccctttgc cccatccctc    2267 ccccgcatcc tcccccgtgg ctcttttcct tagggatctt gccaaggtga tgcttggcag      2327
cccacggtaa aggaaggggg aaaaagatta ggtgggagag agagagagag agagagagag      2387
agagagagag agagagagag agagagagag agagagagag agaaagagag agagatgttt      2447
gagagagggc aaagtggttt caaattttttc caatacattc agaagccgag tgggaagggg    2507
ggctgtgtga cctaacagga cagaactttc tccaattact gggtgactca gctgcactgg     2567
tgactcactt caatgtgtca tttccggctg ctgtaagtga gcagtggaca cgtgggggggg    2627 gggggggtgag gatgaaagaa acagccagct cctggtcaac caccttagtt agataatctt    2687
ttttgaaagc ttcctagctg ggggtatgat cagaaaacca atttactgaa aaactgcaca      2747
ggaaggtaac gtgaatctaa tttcatagcg ggccgctctg catccgttac atctccactg      2807
gaaaaaaata atcattttct ttttgtgtgt gtgtgtgtgt tttagctttt ctccctctcc      2867
ctctttctct ctcatttcat tatgcactgg ataaccatac accgtgtacc acaggggccc     2927
aaatgtgggg tcacatggtc ttgaattttg tggggtacat atgcctttgt ttgtttgttt     2987
tcacttttga tatataaaca ggtaaatgtg ttttttaaaaa ataataaaaa tagagaatat    3047
gcagac                                                                3053
```

<210> SEQ ID NO 14
<211> LENGTH: 402
<212> TYPE: PRT
<213> ORGANISM: Rat

<400> SEQUENCE: 14

```
Met Gln Met Ser Ser Ala Leu Thr Cys Leu Thr Leu Gly Leu Val Leu
1               5                   10                  15

Val Phe Gly Lys Gly Phe Ala Ser Pro Leu Pro Glu Ser His Thr Ala
            20                  25                  30

Gln Gln Ala Thr Asn Phe Gly Val Lys Val Phe Gln His Val Val Gln
        35                  40                  45

Ala Ser Lys Asp Arg Asn Val Val Phe Ser Pro Tyr Gly Val Ser Ser
    50                  55                  60

Val Leu Ala Met Leu Gln Leu Thr Thr Ala Gly Lys Thr Arg Gln Gln
65                  70                  75                  80

Ile Gln Asp Ala Met Gly Phe Asn Ile Ser Glu Arg Gly Thr Ala Pro
                85                  90                  95

Ala Leu Arg Lys Leu Ser Lys Glu Leu Met Gly Ser Trp Asn Lys Asn
            100                 105                 110

Glu Ile Ser Thr Ala Asp Ala Ile Phe Val Gln Arg Asp Leu Glu Leu
        115                 120                 125

Val Gln Gly Phe Met Pro His Phe Phe Lys Leu Phe Arg Thr Thr Val
    130                 135                 140

Lys Gln Val Asp Phe Ser Glu Val Glu Arg Ala Arg Phe Ile Ile Asn
145                 150                 155                 160
```

-continued

```
Asp Trp Val Glu Arg His Thr Lys Gly Met Ile Ser Asp Leu Leu Ala
                165                 170                 175
Lys Gly Ala Val Asn Glu Leu Thr Arg Leu Val Leu Val Asn Ala Leu
            180                 185                 190
Tyr Phe Asn Gly Gln Trp Lys Thr Pro Phe Leu Glu Ala Ser Thr His
        195                 200                 205
Gln Arg Leu Phe His Lys Ser Asp Gly Ser Thr Ile Ser Val Pro Met
    210                 215                 220
Met Ala Gln Asn Asn Lys Phe Asn Tyr Thr Glu Phe Thr Thr Pro Asp
225                 230                 235                 240
Gly His Glu Tyr Asp Ile Leu Glu Leu Pro Tyr His Gly Glu Thr Leu
                245                 250                 255
Ser Met Phe Ile Ala Ala Pro Phe Glu Lys Asp Val Pro Leu Ser Ala
            260                 265                 270
Ile Thr Asn Ile Leu Asp Ala Glu Leu Ile Arg Gln Trp Lys Ser Asn
        275                 280                 285
Met Thr Arg Leu Pro Arg Leu Leu Ile Leu Pro Lys Phe Ser Leu Glu
    290                 295                 300
Thr Glu Val Asp Leu Arg Gly Pro Leu Glu Lys Leu Gly Met Thr Asp
305                 310                 315                 320
Ile Phe Ser Ser Thr Gln Ala Asp Phe Thr Ser Leu Ser Asp Gln Glu
                325                 330                 335
Gln Leu Ser Val Ala Gln Ala Leu Gln Lys Val Lys Ile Glu Val Asn
            340                 345                 350
Glu Ser Gly Thr Val Ala Ser Ser Ser Thr Ala Ile Leu Val Ser Ala
        355                 360                 365
Arg Met Ala Pro Thr Glu Met Val Leu Asp Arg Ser Phe Leu Phe Val
    370                 375                 380
Val Arg His Asn Pro Thr Glu Thr Ile Leu Phe Met Gly Gln Leu Met
385                 390                 395                 400
Glu Pro

<210> SEQ ID NO 15
<211> LENGTH: 16
<212> TYPE: DNA
<213> ORGANISM: Mouse

<400> SEQUENCE: 15
ctagagtcgg ggcggc                                                    16

<210> SEQ ID NO 16
<211> LENGTH: 28
<212> TYPE: DNA
<213> ORGANISM: Mouse

<400> SEQUENCE: 16
cttatcgatt ttaccacatt tgtagagg                                       28
```

THERAPEUTIC METHODS EMPLOYING PAI-1 INHIBITORS AND TRANSGENIC NON-HUMAN ANIMAL FOR SCREENING CANDIDATE PAI-1 INHIBITORS

CROSS REFERENCE TO RELATED APPLICATIONS

This application is based on and claims priority to U.S. Provisional Application Ser. No. 60/358,061, filed Feb. 19, 2002, and entitled THERAPEUTIC METHODS EMPLOYING PAI-1 INHIBITORS AND TRANSGENIC NON-HUMAN ANIMAL FOR SCREENING CANDIDATE PAI-1 INHIBITORS, herein incorporated by reference in its entirety.

TECHNICAL FIELD

The present invention relates, in general, to therapeutic methods for warm-blooded vertebrate animals and to transgenes and non-human transgenic animals. More particularly, the present invention relates to a construct comprising a plasminogen activator inhibitor-1 (abbreviated as PAI-1) gene encoding a biologically active PAI-1 polypeptide and a vector. Also, the present invention relates to a transgenic non-human vertebrate animal having such a PAI-1 gene incorporated into its genome, for instance, a transgenic mouse, and a method of employing such transgenic animals to test candidate compositions to determine if they have PAI-1 inhibition activity. Furthermore, the present invention relates to employing PAI-1 activity-inhibiting compositions in a method of treating warm-blooded vertebrate animals.

Table of Abbreviations

| | |
|---|---|
| ACEI | angiotensin converting enzyme inhibitor |
| AIIRA | angiotensin II receptor antagonist |
| BAC | bacterial artificial chromosome |
| COPD | chronic obstructive pulmonary disease |
| ECM | extracellular matrix |
| µM | micromolar |
| MMP | matrix metallo-protease |
| mPPET-1 | mouse preproendothelin-1 |
| p5.9 | plasmid containing the mouse preproendothelin-1 (mPPET-1) gene promoter |
| PA | plasminogen activator |
| PAI | plasminogen activator inhibitor |
| PAI-1 | plasminogen activator inhibitor-1 |
| PAI-1-stab | stable mutant plasminogen activator inhibitor-1 |
| RCL | reactive center loop |
| tPA | tissue-type PA |
| uPA | urokinase-type PA |
| VN | vitronectin |
| VNBS | VN binding site |
| YAC | yeast artificial chromosome |

BACKGROUND OF THE INVENTION

The plasminogen activator (PA) system has an important role in controlling endogenous fibrosis and regulating the extracellular matrix (ECM) proteolysis relevant to tissue remodeling (Gabazza, E. C., et al., *Lung,* 177:253, 1999). The tissue-type PA (tPA) and urokinase-type PA (uPA) converts plasminogen to plasmin, which enhances proteolytic degradation of the ECM. An important mechanism in the regulation of PA activity is the inhibition of uPA or tPA by three major inhibitors, which are PAI-1, PAI-2, and PAI-3 (Kruithof, E. K., *Enzyme,* 40:113, 1998). Thus, as is well known, the plasminogen activator/plasmin system plays a critical role in fibrinolysis, cellular migration, and matrix remodeling. More specifically, Stefansson and Lawrence, *Nature,* 1996; 383:441–3, describes how PAI-1 blocks cell migration. Furthermore, Nar, et al., *Journal of Molecular Biology,* 2000; 297(3):683–95, describe the structure of PAI-1. Carmeliet, et al., *J. Clin. Invest.,* 1993; 92:2746–2755, describe mice lacking sufficient PAI-1.

To elaborate, plasminogen is converted to its active form, plasmin, by serine proteases tissue-type plasminogen activator (t-PA) and urokinase-type plasminogen activator (u-PA) (Sprengers E D, Kluft C. Plasminogen activator inhibitors. Blood 1987; 69: 381–7). Plasmin has a broad spectrum of proteolytic activities such as degradation of fibrin, activation of matrix metallo-proteases (MMPs) that degrade extracellular matrix (ECM) and play important roles in tissue remodeling. The t-PA activated plasminogen system is primarily responsible for degradation of fibrin. The balance between plasminogen activators (PA) and plasminogen activator inhibitor-1 (PAI-1) predominantly determines the plasma fibrinolytic activity (Rosenberg R D, Aird W C, 1999. Vascular-bed-specific hemostasis and hypercoagulable states. *New England Journal of Medicine.* 340: 1555–1564). The u-PA activated plasminogen system functions in cell migration and tissue remodeling. The activation of plasminogen system is regulated either by inhibition of t-PA or u-PA by plasminogen activator inhibitor type-1 (PAI-1) (Francis R B Jr, Kawanishi D, Baruch T, Mahrer P, Rahimtoola S, Feinstein D I. Impaired fibrinolysis in coronary artery disease. Am Heart J 1988; 115:776–80) or by inhibition of plasmin by $\alpha_2$-antiplasmin (Booth N A. Natural inhibitors of fibrinolysis. In Bloom A L, Forbes C D, Thomas D P and Tuddenham E G D (eds) Haemostasis and Thrombosis, $3^{rd}$ edin, pp699–717. Edinburg: Churchill Livingstone, 1994).

Plasma PAI-1 appears to mainly originate from the vascular endothelium, adipose tissue, and the liver (Loskutoff D J, N Y T, Sawdey M, Lawrence D., *Journal of Cellular Biochemistry,* 1986; 32:273–80; Samad F, Yamamoto K, Loskutoff D J, *Journal of Clinical Investigation* 1996; 97:37–46; Chomiki N, Henry M, Alessi M C, Anfosso F, Juhan-Vague I., *Thrombosis & Haemostasis* 1994; 72:44–53) and large quantities of which is stored by platelets and secreted upon platelet aggregation (Declerck P J, Alessi M C, Verstreken M, Kruithof E K, Juhan-Vague 1, Collen D., *Blood* 1988; 71:220–5). PAI-1 and t-PA exist in plasma in 4:1 molar ratio (Vaughan D E, Rouleau J-L, Ridker P M, Arnold J M O, Menapace F J, Pfeffer M A. Effects of ramipril on plasma fibrinolytic balance in patients with acute anterior myocardial infarction. Circulation 1997; 96:442–447) and PAI-1 in circulation has a $T_{1/2}$ of approximately 5 minutes and is removed via a hepatic clearance mechanism (Vaughan D E, Declerck P J, Van Houtte E, De Mol M, Collen D., *Circulation Research* 1990; 67:1281–6).

Only a fraction of the secreted, active PAI-1 reacts with plasma t-PA, and forms inert, covalent complexes. Majority of PAI-1 in plasma and PAI-1 in the extracellular matrix of blood vessels binds to a 75 kD glycoprotein vitronectin (VN). The PAI-1-vitronectin complex may represent the physiologically relevant form of the inhibitor in the extracellular matrix (Keijer J, Ehrlich H J, Linders M, Preissner K T, Pannekoek H., *Journal of Biol. Chem.* 1991; 266: 10700–7).

PAI-1 production is stimulated by a number of factors such as inflammatory cytokines, e.g. interleukin-I (IL-1) (Emeis J J, Kooistra, T., *Journal of Experimental Medicine* 1986; 163:1260–6) and tumor necrosis factor $\alpha$ (TNF$\alpha$), transforming growth factor β (TGFβ) (Sawdey M, Podor T J, Loskutoff D J. *Journal of Biological Chemistry* 1989; 264:10396–401), epidermal growth factor (EGF), thrombin (Dichek D, Quertermous T. *Blood* 1989; 74:222–8) and insulin (Alessi M C, Juhan-Vague 1, Kooistra T, Declerck P J, Collen D., *Thrombosis & Haemostasis* 1988; 60:491–4). The infusion of endotoxin has also stimulated PAI-1 levels in plasma (Emeis J J, Kooistra. T., *Journal of Experimental Medicine* 1986; 163:1260–6; Colucci M, Paramo J A and Collen D., *J. Clin Invest* 1985; 75:818–24). Angiotensin II (Ang II) and angiotensin IV (Ang IV) also stimulate induction of PAI-1 transcription in vascular tissue in vitro and and in vivo (Vaughan D E, Lazos S A, Tong K., *Journal of Clinical Investigation* 1995; 95:995–1001; Feener E P, Northrup J M, Aiello L P, King G L., *Journal of Clinical Investigation* 1995; 95:1353–62).

The reactive center loop (RCL) of PAI-1 serves as the suicide inhibitory substrate for t-PA and u-PA by forming a covalent complex with PAs after its RCL is cleaved at $^{346}$Arg -$^{347}$Met bond (P1-P1') (Aertgeerts K, De Bondt H L, De Ranter C, Declerck P J., *Journal of Structural Biology* 1994; 113:23 9–45; Kruithof E K; Tran-Thang C, Ransijn A, Bachmann F., *Blood* 1984; 64:907–13). PAI-1 spontaneously acquires a thermodynamically more stable but functionally inactive latent form (Declerck P J, De Mol M, Alessi MC, et al., *Journal of Biological Chemistry* 1988; 263: 15454–61). A series of amino acid substitutions (N150H, K154T, Q301P, Q315L and M354I) resulted in stabilization of reactive center loop of human PAI-1 in the active conformation (referred to as PAI-1-stab) and extended the $T_{1/2}$ of the enzyme from 2.5 hrs to >145 hrs at 37° C. in vitro (M. B. Berkenpas, D. A. Lawrence and D. Ginsburg, *EMBO J.* (1995) 14: 2969–2977). Clinical evidence linking PAI-1 with arterial and venous thrombosis stresses physiological importance of PAI-1 (Wiman B, Ljungberg B, Chmielewska J, Urden G, Blomback M, Johnsson H., *J Lab Clin Med* 1985; 105:265–70; Auwerx, J., Bouillon R, Collen D, Geboers, J., *Arteriosclerosis* 1988; 8:68–72; Margaglione M, Di Minno G, Grandone E, et al., *Arterioscler Thromb* 1994;14:1741–5; Thogersen A M, Jansson J H, Boman K, et al., *Circulation* 1998; 98:2241–7; Juhan-Vague 1, Valadier J, Alessi M C, et al., *Thrombosis & Haemostasis* 1987; 57:67–72).

Despite the above-described efforts, there remains a need in the art for further characterization of the biological role of PAI-1. An animal model to facilitate such characterization is also needed. The present invention addresses these and other needs in the art.

SUMMARY AND OBJECTS OF THE INVENTION

A method of treating a warm-blooded vertebrate animal having a medical condition in need of treatment with a composition that exhibits PAI-1 inhibition activity is disclosed. The method comprises administering a treatment effective amount of the composition to a warm-blooded animal having a medical condition selected from the group consisting of alopecia, undesired weight loss, Alzheimer's Disease, systemic amyloidosis, myelofibrosis, nephrosclerosis, pattern baldness, and combinations thereof; and observing an improvement in the medical condition in the warm-blooded animal having the medical condition.

A transgenic non-human warm-blooded vertebrate animal having incorporated into its genome a PAI-1 gene encoding a biologically active PAI-1 polypeptide is also disclosed. In a preferred embodiment, the PAI-1 gene is present in the genome of the animal in a copy number effective to confer overexpression in the animal of the PAI-1 polypeptide.

A transgene construct comprising an isolated PAI-1 gene encoding a biologically active PAI-1 polypeptide cloned into a vector is also disclosed.

A method of testing a candidate composition for PAI-1 inhibition activity is also disclosed. The method comprises obtaining a transgenic non-human warm blooded vertebrate animal having incorporated into its genome a PAI-1 gene encoding a biologically active PAI-1 polypeptide, the PAI-1 gene being present in the animal's genome in a copy number effective to confer overexpression in the animal of the PAI-1 polypeptide; administering the composition to the animal; and observing the animal for determination of a change in the animal indicative of inhibition of the activity of PAI-1.

Accordingly, it is an object of the invention to provide a novel method of treating disorders with a PAI-1 activity-inhibiting composition. It is another object to provide a transgenic animal having a PAI gene incorporated into its genome to confer overexpression of PAI-1, as well as a method of using the animal for testing candidate compositions to determine if they are effective for inhibiting PAI-1 biological activity. These and other objects are achieved in whole or in part by the present invention.

Some of the objects of the invention having been stated above, other objects will become evident as the description proceeds, when taken in connection with the accompanying Figures and Examples as best described below.

DETAILED DESCRIPTION OF THE INVENTION

Figure 1:
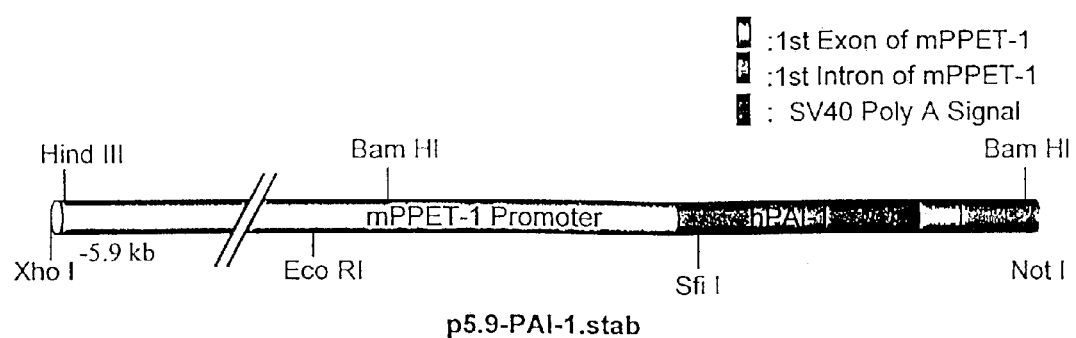
FIG. 1 depicts a preferred embodiment of a stable PAI-1 transgene construct.

The present invention pertains in part to the pathological consequences of impaired activation of plasminogen system by chronic overexpression of active human PAI-1 under the control of mPPET-1 promoter. Disclosed herein is the remarkable phenotypic alterations exhibited by newly engineered lines of transgenic mice that overexpress a stable variant of human PAI-1 under the control of the mPPET-1 promoter. These transgenic animals manifest time-dependent alopecia areata, hepatosplenomegaly, and evidence of extramedullary hematopoeisis. Microscopic examination of the spleen and liver reveals that enlargement and architectural disruption in both organs are due to extracellular matrix and amyloid deposition, and in spleen, also due to hematopoetic precursors (including megakaryocytes). These animals also exhibit glomerulosclerosis and renal fibrosis. Taken together, these findings indicate that PAI-1 influences a broad spectrum of processes involving cellular migration and matrix proteolysis, which findings are useful for determining the pathogenesis and providing the treatment of disorders as complex as systemic amyloidosis and myelofibrosis, and as pervasive as pattern baldness.

Thus, the present invention provides, in one embodiment, therapeutic methods for treating vascular thrombic disorders, asthma, chronic obstructive pulmonary disease, Alzheimer's Disease, myelofibrosis, wasting disorders characterized by weight loss (e.g. anorexia, AIDS, etc.), systemic amyloidosis, alopecia, male pattern baldness, glomerulosclerosis, keloids, apocrine cysts, acne, atherosclerosis, aging, a wound, and combinations thereof, in subjects in need of such treatment.

In another embodiment, the present invention provides a transgenic non-human vertebrate animal having a PAI-1 gene incorporated into its genome. Preferably, the incorporation of the PAI-1 gene results in the overexpression of PAI-1 in the animal. More preferably, the animal is a transgenic mouse. Also provided is a construct comprising a PAI-1 gene encoding a biologically active PAI-1 polypeptide and a vector. The construct is preferably employed in the production of the transgenic non-human animal of the present invention.

In yet another embodiment, the present invention provides a method of employing such transgenic animals to test candidate compositions to determine if they have PAI-1 inhibition activity.

Before the present therapeutic methods as well as the present transgenic animals and uses thereof are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and", and "the" include plural referents unless the context clearly dictates otherwise. Thus, for example, reference to "a construct" includes a plurality of such constructs and reference to "the PAI-1-encoding nucleic acid" includes reference to one or more PAI-1-encoding nucleic acids and to equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

I. Definitions

"Antibodies" refers to whole antibodies and antibody fragments or molecules including antibody fragments, including, but not limited to, single chain antibodies, humanized antibodies, and Fab, F(ab')$_2$, V$_h$, V$_l$, Fd, and single or double chain Fv fragments.

The term "medical condition associated with PAI-1 biological activity" can include any medical condition associated with PAI-1 biological activity. Preferably, this term includes but is not limited to a medical condition selected from the group consisting of vascular thrombic disorders, asthma, chronic obstructive pulmonary disease (COPD), alopecia, undesired weight loss (such as associated with anorexia or with a disease characterized by wasting—e.g., AIDS), Alzheimer's Disease, nephrosclerosis (including but not limited to glomerulosclerosis), arteriosclerosis (such as atherosclerosis), systemic amyloidosis, myelofibrosis, pattern baldness (e.g., male or female), keloids, apocrine cysts, acne, aging, a wound, and combinations thereof. Glomerulosclerosis includes but is not limited to diabetic and non-diabetic glomerulosclerosis.

The term "phenomena associated with PAI-1 biological activity" can include any phenomena associated with PAI-1 biological activity, including those observed in a medical condition associated with PAI-1 biological activity. Representative phenomena include but are not limited to hair loss, hepatosplenomegaly, extramedullary hematopoeisis, systemic amyloid deposition, cerebral amyloid deposition, and combinations thereof.

The term "aging" is meant to include all physiological effects of the process of aging, including effects on brain and mental function as well as physical appearance and condition. By way of additional example, "skin aging" includes skin atrophy and means the thinning and/or general degradation of the dermis caused by free radical damage that is often characterized by an alteration and degeneration of collagen and/or elastin. In epidermis, markers of degeneration include lipofuscin granules and loss of rete pegs. Skin aging may be caused by either intrinsic or extrinsic factors such as natural chronoaging, photodamage, burns, or chemical damage.

The term "transgene" is used herein to describe genetic material that has been or is about to be artificially inserted into the genome of a warm-blooded vertebrate animal, particularly a cell of a living animal.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "transgenic animal" is meant a non-human animal, usually a mammal (e.g., mouse, rat, rabbit, hamster, etc.), having a non-endogenous (i.e., heterologous) nucleic acid sequence present as an extrachromosomal element in a portion of its cells or stably integrated into its germ line DNA (i.e., in the genomic sequence of most or all of its cells). A heterologous nucleic acid is introduced into the germ line of such transgenic animals by genetic manipulation of, for example, embryos or embryonic stem cells of the host animal.

A "knock-out" of a gene means an alteration in the sequence of the gene that results in a decrease of function of the target gene, preferably such that target gene expression is undetectable or insignificant. A knock-out of an endogenous PAI-1 gene means that function of the PAI-1 gene has been substantially decreased so that expression is not detectable or only present at insignificant levels. "Knock-out" transgenics can be transgenic animals having a heterozygous knock-out of the PAI-1 gene or a homozygous knock-out of the PAI-1 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic)) of the target gene, e.g., by introduction of an additional copy of the target gene, or by operatively inserting a regulatory sequence that provides for enhanced expression of an endogenous copy of the target gene.

"Knock-in" transgenics of interest for the present invention can be transgenic animals having a knock-in of the animal's endogenous PAI-1. Such transgenics can be heterozygous knock-in for the PAI-1 gene, homozygous for the knock-in of the PAI-1 gene. "Knock-ins" also encompass conditional knock-ins as defined above.

By "construct" is meant a recombinant nucleic acid, generally recombinant DNA, which has been generated for the purpose of the expression of a specific nucleotide sequence(s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a PAI-1 sequence).

The term "subject" as used herein refers to any invertebrate or vertebrate species. The methods of the present invention are particularly useful in the treatment of warm-blooded vertebrates. Thus, in a preferred embodiment, the invention concerns mammals and birds.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

II. Therapeutic Methods

A method of treating a warm-blooded vertebrate animal having a medical condition in need of treatment with a composition that exhibits PAI-1 inhibition activity is provided in accordance with the present invention. In a preferred embodiment the method comprises administering a treatment effective amount of the composition to a warm-blooded animal having a medical condition selected from one group consisting of alopecia, undesired weight loss, Alzheimer's Disease, systemic amyloidosis, myelofibrosis, pattern baldness, nephrosclerosis (including but not limited to glomerulosclerosis), arteriosclerosis (such as atherosclerosis), systemic amyloidosis, myelofibrosis, male pattern baldness, keloids, apocrine cysts, acne, aging, a wound, and combinations thereof and observing an improvement in the medical condition in the warm-blooded animal having the medical condition. Thus, although it is not applicants' desire to be bound by any particular theory of operation, the observation of an improvement in the medical condition is believed to indicative of inhibition activity of PAI-1.

Animals so treated can be warm-blooded vertebrates, for instance, mammals and birds. More particularly, the animal can be selected from the group consisting of rodent, swine, bird, ruminant, and primate. Even more particularly, the animal can be selected from the group consisting of a mouse, a rat, a pig, a guinea pig, poultry, an emu, an ostrich, a goat, a cow, a sheep, and a rabbit. Most particularly, the animal can be a primate, such as an ape, a monkey, a lemur, a tarsier, a marmoset, or a human.

Thus, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

The medical condition can include, but is not limited to a medical condition selected from the group consisting of alopecia, undesired weight loss, Alzheimer's Disease, systemic amyloidosis, myelofibrosis, pattern baldness, and combinations thereof.

II.A. PAI-1 Modulators

PAI-1 modulators are used in the present methods for modulating PAI-1 activity in cells and tissues. Thus, as used herein, the terms "modulate", "modulating", and "modulator" are meant to be construed to encompass inhibiting, blocking, promoting, stimulating, agonising, antagonizing, or otherwise affecting PAI-1 activity in cells and tissues. PAI-1 modulators also include substances that inhibit or promote expression of a PAI-1 encoding nucleic acid segment.

In a preferred embodiment, a PAI-1 activity inhibiting composition is employed in accordance with the present invention. The terms "composition exhibiting PAI-1 inhibition activity", "PAI-1 inhibitor" or "PAI-1 inhibiting composition" are used interchangeably and are meant to refer to a substance that acts by inhibiting, blocking, antagonizing, down-regulating or otherwise reducing PAI-1 activity in cells and tissues. These terms also encompass substance that inhibits expression of a PAI-1 encoding nucleic acid segment, e.g. an anti-sense oligonucleotide or small molecule that blocks the promoter of the PAI-1 gene.

Representative PAI-inhibitors are disclosed in U.S. Pat. No. 5,980,938 to Berg et al. (assignee Eli Lilly and Co.), which discloses methods of inhibiting PAI-1 using benzopyran compounds. Butadiene derivatives having PAI-1 inhibitory activity and a process for preparing the same are disclosed in the U.S. Pat. No. 6,248,743 to Ohtani et al. (assignee Tanabe Seiyaku Co.). PCT International Publication No. WO0151085 by Demissie-Sanders et al. (assignee Tanox Inc.) discloses PAI-1 antagonists and their use in the treatment of asthma and chronic obstructive pulmonary disease. Representative PAI-1 inhibitors also include peptide therapeutic agents, such as those disclosed in U.S. Pat. No. 5,639,726 to Lawrence et al. (co-assignees The Regents of the University of Michigan and Henry Ford Health System), which discloses peptides that decrease the half-life of active PAI-1.

Antagonists to PAI-1 can be used in the treatment of the above-noted medical conditions associated with PAI-1 biological activity. Antagonists can be antibodies, peptides, proteins, nucleic acids, small organic molecules, or polymers. In one embodiment the antagonist is an antibody. The antibody can be a monoclonal or polyclonal antibody. The antibody can be chemically linked to another organic or bio-molecule. Monoclonal and polyclonal antibodies can be made by any method generally known to those of ordinary skill in the art. For example, U.S. Pat. No. 5,422,245 to Nielsen et al. (assignee: Fonden Til Fremme AF Eksperimental Cancerforskning of Copenhagen, Denmark) describes the production of monoclonal antibodies to plasminogen activator inhibitor.

Peptides, proteins, nucleic acids, small organic molecules, and polymers can be identified by combinatorial methods.

Known PAI-1 antagonists can be used, for example spironolactone, imidapril, angiotensin converting enzyme inhibitors (ACEI, captopril, or enalapril), angiotensin II receptor antagonist (AIIRA), or defibrotide (a polydeoxyribonucleotide).

A PAI-1 inhibitor or antagonist is preferably administered at a therapeutically effective dose or concentration. Representative concentrations of the inhibitor or antagonists are preferably less than about 10 µM, about 1 µM, about 0.1 µM, about 0.01 µM about 0.001 µM, or about 0.0001 µM.

The therapeutic methods of the present invention are also directed towards the use of compounds that change the concentration of upstream regulators or downstream effector molecules of PAI-1, in treating or preventing the above-listed medical conditions associated with PAI-1. In one embodiment, the method can comprise selecting a warm-blooded vertebrate subject diagnosed with a medical condition associated with PAI-1 biological activity, and administering to the warm-blooded vertebrate subject one or more compounds. Representative compounds can comprise urokinase, tissue plasminogen activator, vitronectin, plasminogen, plasmin, matrix metalloproteinases, or tissue inhibitors of metalloproteinases. Representative concentrations for the compound include but are not limited to less than about 100 µM, about 10 µM, about 1 µM, about 0.1 µM, about 0.01 µM, about 0.001 µM or about 0.0001 µM.

An additional embodiment of the invention is directed towards a method for the prevention of a medical condition associated with PAI-1 biological activity. The method can comprise selecting a warm-blooded vertebrate subject in which the prevention of a medical condition associated with the biological activity of PAI-1 is desired and administering to the warm-blooded vertebrate subject a PAI-1 inhibiting composition in an amount sufficient to reduce the occurrence or effects of the medical condition associated with PAI-1 biological activity relative to a warm-blooded vertebrate subject that did not receive such administration. Preferably, the concentration of the PAI-1 inhibiting composition is less than about 100 µM, about 10 µM, about 1 µM, about 0.1 µM, about 0.01 µM, about 0.001 µM or about 0.0001 µM.

II.B. Formulation of Therapeutic Compositions

The PAI-1 biological activity modulating substances, gene therapy vectors, and substances that inhibit or promote expression of a PAI-1 encoding nucleic acid segment are adapted for administration as a pharmaceutical composition. Additional formulation and dose preparation techniques have been described in art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT International Publication Number WO 93/25521 of Johnson et al. published Dec. 23, 1993, the entire contents of each of which are herein incorporated by reference.

For therapeutic applications, a treatment effective amount of a composition of the invention is administered to a subject. A "treatment effective amount" is an amount of therapeutic composition sufficient to produce a measurable biological response, such as but not limited to a reduction in PAI-1 biological activity. Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, and the physical condition and prior medical history of the subject being treated. Preferably, a minimal dose is administered; and dose is escalated in the absence of dose-limiting toxicity. Determination and adjustment of a therapeutically effective dose, as well as evaluation of when and how to make such adjustments, are well known to those of ordinary skill in the art of medicine.

For the purposes described above, the identified substances can normally be administered systemically or partially, usually by oral or parenteral administration. The doses to be administered are determined depending upon age, body weight, symptom, the desired therapeutic effect, the route of administration, and the duration of the treatment, etc.; one of skill in the art of therapeutic treatment will recognize appropriate procedures and techniques for determining the appropriate dosage regimen for effective therapy. Various compositions and forms of administration are contemplated and are generally known in the art. Other compositions for administration include liquids for external use, and endermic linaments (ointment, etc.), suppositories and pessaries that comprise one or more of the active substance(s) and can be prepared by known methods.

Thus, the present invention provides pharmaceutical compositions comprising a polypeptide, polynucleotide, antibody or fragment thereof, small molecule or compound of the present invention and a physiologically acceptable carrier. More preferably, a pharmaceutical composition comprises a compound discovered via the screening methods described herein.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred approach for purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g., injected intra-vascularly).

III. Transgenic Non-Human Animals

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell.

Vectors for stable integration include plasmids, retroviruses and other animal viruses, bacterial artifical chromosomes (BACs), yeast artificial chromosomes (YACs), cosmids and the like. The term "vector", as used herein refers to a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of a PAI-1 polypeptide, as described further herein below. Preferred vectors include but are not limited p5.9.

Useful animals should be warm-blooded non-human vertebrates, for instance, mammals and birds. More particularly, the animal can be selected from the group consisting of rodent, swine, bird, ruminant, and primate. Even more particularly, the animal can be selected from the group consisting of a mouse, a rat, a pig, a guinea pig, poultry, an emu, an ostrich, a goat, a cow, a sheep, and a rabbit. Of interest are transgenic mammals, e.g. cows, pigs, goats, horses, etc., and particularly rodents, e.g. rats, mice, etc. Preferably, the transgenic animals are mice.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene can be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which can be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

In general, the transgenic animals of the invention comprise genetic alterations to provide for (Sprengers E D, Kluft C. Plasminogen activator inhibitors. Blood 1987; 69: 381–7) expression of a biologically active PAI-1 polypeptide, and/or (Rosenberg R D, Aird W C, 1999. Vascular-bed-specific hemostasis and hypercoagulable states. *New England Journal of Medicine.* 340:1555–1564) expression of a desired biologically active PAI-1 sequence (e.g., human PAI-1). Preferably, the introduced sequences provide for high expression of PAI-1 so that overexpression of the PAI-1 gene is conferred in the transgenic animal. Thus, preferably, the PAI-1 transgene is overexpressed in the host animal, that is the transgene provides for increased levels of PAI-1 production relative to wild-type, e.g., more particularly a level of PAI-1 expression to facilitate onset of a medical condition associated with PAI-1 biological activity and/or the observation of phenomena associated with PAI-1 biological activity.

The transgenic animals of the invention can comprise other genetic alterations in addition to the presence of the PAI-i-encoding sequence. For example, the host's genome can be altered to affect the function of endogenous genes (e.g., endogenous PAI-1 gene), contain marker genes, or other genetic alterations consistent with the goals of the present invention.

III.A. Knockouts and Knockins

Although not necessary to the operability of the invention, the transgenic animals described herein can also comprise alterations to endogenous genes in addition to (or alternatively for PAI-1), to the genetic alterations described above. For example, the host animals can be either "knockouts" and/or "knockins" for a target gene(s) as is consistent with the goals of the invention (e.g., the host animal's endogenous PAI-1 can be "knocked out" and/or the endogenous PAI-1 gene "knocked in"). Knockouts have a partial or complete loss of function in one or both alleles of an endogenous gene of interest (e.g., PAI-1). Knockins have an introduced transgene with altered genetic sequence and/or function from the endogenous gene. The two can be combined, for example, such that the naturally occurring gene is disabled, and an altered form introduced. For example, it can be desirable to knockout the host animal's endogenous PAI-1 gene, while introducing an exogenous PAI-1 gene (e.g., a human PAI-1 gene).

In a knockout, preferably the target gene expression is undetectable or insignificant. For example, a knockout of an PAI-1 gene means that function of the PAI-1 has been substantially decreased so that expression is not detectable or only present at insignificant levels. This can be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches can also be used to achieve the "knockout". A chromosomal deletion of all or part of the native gene can be induced, including deletions of the non-coding regions, particularly the promoter region, 3' regulatory sequences, enhancers, or deletions of gene that activate expression of PAI-1 genes. A functional knock-out can also be achieved by the introduction of an anti-sense construct that blocks expression of the native genes (for example, see Li and Cohen (1996) *Cell* 85:319–329). "Knockouts" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

It should be noted that while a PAI-1 and/or host PAI-1 gene can be knocked out in the transgenic animals of the invention, it is not necessary to the utility of the transgenic PAI-1 animal. Indeed, it is envisioned that PAI-1 knockout transgenic animals would primarily serve as a control animal in, for example, the drug screening assays disclosed herein below.

A "knockin" of a target gene means an alteration in a host cell genome that results in altered expression or function of a native target gene. Increased (including ectopic) or decreased expression can be achieved by introduction of an additional copy of the target gene, or by operatively inserting a regulatory sequence that provides for enhanced expression of an endogenous copy of the target gene. These changes can be constitutive or conditional, i.e. dependent on the presence of an activator or repressor. The use of knockin technology can be combined with production of exogenous sequences to produce the transgenic animals of the invention. For example, the PAI-1 transgenic animals of the invention can contain a knockin of the host's endogenous PAI-1-encoding sequences to provide for the desired level of PAI-1 expression, and can contain an exogenous PAI-1-encoding sequence.

III.B. Nucleic Acid Compositions

Constructs for use in the present invention include any construct suitable for use in the generation of transgenic animals having the desired levels of expression of a desired PAI-1-encoding sequence. Methods for isolating and cloning a desired sequence, as well as suitable constructs for expression of a selected sequence in a host animal, are well known in the art. The construct can include sequences other than the PAI-1-encoding sequences. For example, a detectable marker, such as lac Z can be included in the construct, where upregulation of expression of the encoded sequence will result in an easily detected change in phenotype.

The PAI-1-encoding construct can contain a wild-type sequence encoding PAI-1 or a mutant sequence encoding PAI-1 (providing the PAI-1 sequence, when expressed in conjunction with PAI-1 in the host animal, impacts cellular migration and matrix proteolysis, which play a role in the pathogenesis and treatment of disorders as complex as systemic amyloidosis and myelofibrosis, and as pervasive as male pattern baldness). Likewise, the PAI-1-encoding construct can contain a wild-type PAI-1-encoding sequence or a sequence encoding a modified PAI-1, particularly where the-modification provides for a desired level of PAI-1 expression. Regardless of the precise construct used, the encoded PAI-1 should preferably be a biologically active form of a PAI-1 polypeptide.

The term "PAI-1 gene" is used generically to mean PAI-1 genes, e.g. homologs from rat, human, mouse, guinea pig, etc., and their alternate forms. A human PAI-1 gene is a preferred PAI-1 gene. "PAI-1 gene" is also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding PAI-1 can be cDNA or genomic DNA or a fragment thereof. The genes can be introduced into an appropriate vector for extrachromosomal maintenance or for integration into the host.

The genomic sequences of particular interest comprise the nucleic acid present between the initiation codon and the stop codon, including all of the introns that are normally present in a native chromosome. They can further include the 3' and 5' untranslated regions found in the mature mRNA. They can further include specific transcriptional and translational regulatory sequences, such as promoters, enhancers, etc., including about 1 kb, but possibly more, of flanking genomic DNA at either the 5' or 3' end of the transcribed region. The genomic DNA can be isolated as a fragment of 100 kb or smaller; and substantially free of flanking chromosomal sequence.

The sequences of the 5' regions of the PAI-1 gene, and further 5' upstream sequences and 3' downstream sequences, can be utilized for promoter elements, including enhancer-binding sites, which provide for expression in tissues where PAI-1 is normally expressed. The tissue specific expression is useful for providing promoters that mimic the native pattern of expression. Naturally occurring polymorphisms in the promoter region are useful for determining natural variations in expression, particularly those that can be associated with disease. For example, the most significant of these is a single guanosine insertion/deletion variation (5G or 4G) in the promoter region (4G deletion polymorphism), situated 675 base pairs upstream from the transcriptional start site of the PAI-1 gene. The 4G allele is correlated with increased plasma PAI-1 levels. See Dawson, S. J., et al., *J. Biol. Chem.*, 268:10739,1993; Hermans, P. W., et al., *Lancet*, 354:556, 1999; Dawson, S., et al., *Arteriosclero. Thromb.*, 11:183, 1991; Mansfield, M., et al., *Thromb. Haemost.*, 71:731,1994.

Alternatively, mutations can be introduced into the promoter region to determine the effect of altering expression in experimentally defined systems. Methods for the identification of specific DNA motifs involved in the binding of transcriptional factors are known in theart, e.g. sequence similarity to known binding motifs, gel retardation studies, etc. For examples, see Blackwell et al. (1995) *Mol Med* 1:194–205; Mortlock et al. (1996) *Genome Res.* 6:327–33; and Joulin and Richard-Foy (1995) *Eur J Biochem* 232: 620–626.

The nucleic acid compositions used in the subject invention can encode all or a part of PAI-1 as appropriate. Fragments can be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

Several isoforms and homologs of PAI-1 have been isolated and cloned. Additional homologs of cloned PAI-1 and/or PAI-1 are identified by various methods known in the art. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under more stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes can be any species, e.g. primate, rodents, canines, felines, bovines, ovines, equines, etc.

Where desirable, the PAI-1 sequences, including flanking promoter regions and coding regions, can be mutated in various ways known in the art to generate targeted changes in the sequence of the encoded protein, splice variant production, etc. The sequence changes can be substitutions, insertions or deletions. Deletions can include large changes, such as deletions of a domain or exon. Other modifications of interest include epitope tagging, e.g. with the FLAG system, HA, etc. For studies of subcellular localization, fusion proteins with green fluorescent proteins (GFP) can be used. Such mutated genes can be used to study structure-function relationships of PAI-1, or to alter properties of the proteins that affect their function or regulation. The PAI-1 encoding sequence can also be provided as a fusion protein. Methods for production of PAI-1 constructs are well known in the art (see, e.g., Wyss-Coray et al. (1995) *Am. J. Pathol.* 147:53–67).

Techniques for in vitro mutagenesis of cloned genes are known. Examples of protocols for scanning mutations can be found in Gustin et al., 1993 *Biotechniques* 14:22; Barany, 1985 *Gene* 37:111–23; Colicelli et al., 1985 *Mol Gen Genet* 199:537–9; and Prentid et al., 1984 Gene 29:303–13. Methods for site specific mutagenesis can be found in Sambrook et al., 1989 *Molecular Cloning: A Laboratory Manual*, CSH Press, pp. 15.3–15.108; Weiner et al., 1993 Gene 126:35–41; Sayers et al., 1992 *Biotechniques* 13:592–6; Jones and Winistorfer, 1992 *Biotechniques* 12:528–30; Barton et al., 1990 *Nucleic Acids Res* 18:7349–55; Marotti and Tomich, 1989 *Gene Anal Tech* 6:67–70; and Zhu 1989 *Anal Biochem* 177:120–4.

The PAI-1 gene, and exemplary derivatives thereof suitable for use in the production of the transgenic animals of the invention can be either genomic or cDNA, preferably cDNA, and can be derived from any source, e.g., human, murine, porcine, bovine, etc. Several PAI-1 sequences have been isolated, cloned, and sequenced. Table 1 provides a list of PAI-1 sequences that can be suitable for use in the present invention, as well as GenBank accession numbers relating to such sequences.

TABLE 1

| PAI-1 Sequence | Reference or GenBank Accession No. |
|---|---|
| Human PAI-1 | X04744 (SEQ ID NO:3) Human mRNA AH002922 Human plasminogen activator inhibitor 1 (PAI-1) gene M16006 (SEQ ID NO:2) Human plasminogen activator inhibitor-1 (PAI-1) mRNA, complete cds |
| Bovine PAI-1 | X16383 (SEQ ID NO:1) Bovine mRNA |
| Rat PAI-1 | M24067 (SEQ ID NO:7) *Rattus norvegicus* plasminogen activator inhibitor-1 (PAI-1) mRNA, complete cds |
| Mink PAI-1 | X58541 (SEQ ID NO:4) Mink mRNA |
| Mouse PAI-1 | NM 008871 (SEQ ID NO:5) *Mus musculus* plasminogen activator inhibitor, type I M33960 (SEQ ID NO:6) Mouse plasminogen activator inhibitor (PAI-1) mRNA, complete cds |

The host animals can be homozygous or heterozygous for the PAI-1-encoding sequence, preferably homozygous. The PAI-1 gene can also be operably linked to a promoter to provide for a desired level of expression in the host animal and/or for tissue-specific expression. Expression of PAI-1 can be either constitute or inducible, preferably constitutive. Preferably, PAI-1 gene expression is driven by a strong promoter, preferably mouse preproendothelin-1 (mPPET-1) gene promoter.

Indeed, in general terms, a preferred embodiment, the transgene of the present invention was prepared in the following manner. The stable human PAI-1 gene was cloned into a plasmid containing the mouse preproendothelin-1 (mPPET-1) gene promoter (5.9 kb). The Xho I-Not I restriction enzyme digest fragment of p5.9-PAI-1.stab was used for microinjections to generate the transgenic mouse. See FIG. 1.

Preferably, the PAI-1 transgenic animals overproduce biologically active PAI-1 relative to control, non-transgenic animals. For example, PAI-1 transgenic animals preferably exhibit PAI-1 mRNA levels in blood, skin, heart, lung, aorta, bone marrow, pancreas, kidney, brain, liver and/or spleen that are greater than PAI-1 mRNA levels in blood, skin, heart, lung, aorta, bone marrow, pancreas, kidney, brain, liver and/or spleen of non-transgenic animals. Preferably, the PAI-1 mRNA levels in blood, skin, heart, lung, aorta, pancreas, kidney, brain, liver and/or spleen are elevated by about one- to two-fold in heterozygous PAI-1 animals, and about five-to six-fold in homozygous PAI-1 animals, relative to PAI-1 mRNA levels in non-transgenic control animals (e.g., in littermate control animals). Methods for assessment of PAI-1 mRNA levels, as well as other methods for assessing PAI-1 production and activity are well known in the art.

III.D. Methods of Making Transgenic Animals

It is thus within the scope of the present invention to prepare a transgenic non-human animal that expresses, and preferably overexpresses, a PAI-1 gene. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding a PAI-i gene product are injected into fertilized mouse eggs. The injected eggs are implanted in pseudo pregnant females and are grown to term to provide transgenic mice whose cells express a PAI-1 gene product.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line can be employed, or embryonic cells can be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they can be used to produce transgenic animals. After transformation, the cells are plated onto a feeder layer in an appropriate medium. Cells containing the construct can be detected by employing a selective medium. After sufficient time for colonies to grow, they are picked and analyzed for the occurrence of homologous recombination or integration of the construct. Those colonies that are positive can then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

A transgenic animal of the present invention can also comprise a mouse with targeted modification of the PAI-1 gene. Mice strains with complete or partial functional inactivation of the PAI-1 gene in all somatic cells are generated using standard techniques of site-specific recombination in murine embryonic stem cells. See Capecchi (1989) *Science* 244(4910):1288–1292; Thomas & Capecchi (1990) *Nature* 346(6287):847–850.

Alternative approaches include the use of anti-sense or ribozyme PAI-1 constructs, driven by a universal or tissue-specific promoter, to reduce levels of PAI-1 in somatic cells, thus achieving a "knock-down" of individual isoforms (Luyckx et al. (1999) *Proc Natl Acad Sci USA* 96(21):12174–12179). The invention also provides the generation of murine strains with conditional or inducible inactivation of the PAI-1 gene (Sauer (1998) *Methods* 14(4): 381–392; Ding et al. (1997) *J Biol Chem* 272(44):28142–28148).

The present invention also provides mice strains with specific "knocked-in" modifications in the PAI-1 gene. This includes mice with genetically and functionally relevant point mutations in the PAI-1 gene, in addition to manipulations such as the insertion of specific repeat expansions.

IV. Drug Screening Assays

A method of testing a candidate composition for PAI-1 inhibition activity is also provided in accordance with the present invention. A wide variety of assays can be used for this purpose, e.g. determination of the localization of drugs after administration, immunoassays to detect amyloid deposition, and the like. Depending on the particular assay, whole animals can be used, or cells derived therefrom. Cells can be freshly isolated from an animal, or can be immortalized in culture. Cells of particular interest are derived from blood, bone marrow, skin, heart, lung, aorta, pancreas, kidney, brain, liver and/or spleen.

In a preferred embodiment, the method comprises obtaining a transgenic non-human warm blooded vertebrate animal having incorporated into its genome a PAI-1 gene encoding a biologically active PAI-1 polypeptide, the PAI-1 gene being present in the genome in a copy number effective to confer overexpression in the transgenic non-human animal of the PAI-1 polypeptide; administering a candidate composition to the transgenic non-human animal; and observing the transgenic non-human animal for determination of a change (preferably an ameliorating change) in the transgenic non-human animal indicative of inhibition of the activity of PAI-1.

In one embodiment the observed change is a change in a phenomena associated with PAI-1 biological activity. The medical condition can include, but is not limited to a medical condition selected from the group consisting of hair loss, hepatosplenomegaly, extramedullary hematopoeisis, renal fibrosis, systemic amyloid deposition, vascular thrombic disorders, asthma, chronic obstructive pulmonary disease (COPD), alopecia, undesired weight loss (such as associated with anorexia or with a disease characterized by wasting—e.g., AIDS), Alzheimer's Disease, nephrosclerosis (including but not limited to glomerulosclerosis), arteriosclerosis (such as atherosclerosis), systemic amyloidosis, myelofibrosis, pattern baldness (e.g., male or female), keloids, apocrine cysts, acne, aging, a wound, and combinations thereof.

The transgenic animal is useful for testing candidate compositions to determine if they are effective as medicaments for treating various medical conditions by inhibiting PAI-1 expression in warm-blooded vertebrate animals having one or more of the medical conditions. For example, the transgenic animal exhibits a medical condition, such as alopecia. Then, a candidate composition, that possibly has PAI-1 inhibition activity, is administered to the animal. Next, the animal is observed to determine whether a change occurs that is indicative of inhibition of PAI-1 activity. In this instance, the hoped for ameliorating change is the growth of hair or the reduction or prevention of hair loss. If the ameliorating change does occur, then the composition is likely useful as a medicament in a method for treating an animal having a medical condition, such as alopecia.

A number of assays are known in the art for determining the effect of a drug on medical conditions and phenomena associated with PAI-1 biological activity. Some examples are provided above, although it will be understood by one of skill in the art that many other assays can also be used. The subject animals themselves are preferably used, alone or in combination with control animals. Control animals can have, for example, a wild-type PAI-1 transgene that is not overexpressed, or can be PAI-1 "knockout" transgenics.

The screen using the transgenic animals of the invention can employ any phenomena associated with PAI-1 biological activity that can be readily assessed in an animal model. The screening can include assessment of phenomena including, but not limited to: 1) analysis of molecular markers (e.g., levels of expression of PAI-1 gene products in blood, skin, heart, lung, aorta, pancreas, kidney, brain, liver and/or spleen); and 2) measurement of PAI-1 activity in plasma or tissues.

Thus, through use of the subject transgenic animals or cells derived therefrom, one can identify ligands or substrates that modulate medical conditions associated with PAI-1 biological activity. Of particular interest are screening assays for candidate compositions that have a low toxicity for human cells.

The term "candidate composition" as used herein describes any molecule, e.g. protein or pharmaceutical, with the capability of affecting the molecular and clinical phenomena associated with PAI-1 activity. Generally pluralities of assay mixtures are run in parallel with different candidate composition concentrations to obtain a differential response to the various concentrations. Typically, one of these concentrations serves as a negative control, i.e. at zero concentration or below the level of detection.

Candidate compositions encompass numerous chemical classes, though typically they are organic molecules, preferably small organic compounds having a molecular weight of more than 50 and less than about 2,500 daltons. Candidate compositions comprise functional groups necessary for structural interaction with proteins, particularly hydrogen bonding, and typically include at least an amine, carbonyl, hydroxyl or carboxyl group, preferably at least two of the functional chemical groups. The candidate compositions often comprise cyclical carbon or heterocyclic structures and/or aromatic or polyaromatic structures substituted with one or more of the above functional groups. Candidate compositions are also found among biomolecules including, but not limited to: peptides, saccharides, fatty acids, steroids, purines, pyrimidines, derivatives, structural analogs or combinations thereof.

Candidate compositions are obtained from a wide variety of sources including libraries of synthetic or natural compounds. For example, numerous approaches are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical approaches, and can be used to produce combinatorial libraries. Known pharmacological agents can be subjected to directed or random chemical modifications, such as acylation, alkylation, esterification, amidification, etc. to produce structural analogs.

EXAMPLES

The following Examples have been included to illustrate preferred modes of the invention. Certain aspects of the following Examples are described in terms of techniques and procedures found or provided by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Materials and Methods Employed In Examples

Construction of Transgene and Generation of Transgenic Mice. The plasmids p5.9Luc and pET2.5 carrying a 5.9 kb and 1.4 kb upstream sequences of mouse preproendothelin-1 (mPPET-1) gene promoter respectively, were a gift from Dr. T. Quertermus. Harats et al. have shown that mPPET-1 promoter is specifically expressed in the endothelial cells of vascular wall as well as other tissues (Harats D, Kurihara H, Belloni P, Oakley H, Ziober A, Ackley D, Cain G, Kurihara Y, Lawn R, and Sigal E, Targeting Gene Expression to the Vascular Wall in Transgenic Mice Using the Murine Preproendothelin-1 Promoter, *J. Clinical Investigation*, 95: 1335–1344, 1995). As discussed above, a series of amino acid substitutions (N150H, K154T, Q301P, Q315L and M3541) resulted in stabilization of reactive center loop of human PAI-1 in the active conformation (referred to as PAI-1-stab) and extended the $T_{1/2}$ of the enzyme from 2.5 hrs to >145 hrs at 37° C. in vitro (M. B. Berkenpas, D. A. Lawrence and D. Ginsburg. Molecular evolution of plasminogen activator-1 functional stability, *EMBO J.* (1995) 14: 2969–2977).

The coding domain sequences for stable PAI-1 were amplified by PCR from the plasmid pMaPAI-1.stab using the high fidelity BIO-X-ACT™ DNA polymerase enzyme (Bioline of Springfield, N.J.), and introducing Bam HI site at the 5'-end and a Bgl II site at the 3'-end and then ligated into pGEM-T EASY™ vector (Promega of Madison, Wis.). Subsequently, the fragment coding for the PAI-1 signal peptide was restored by subcloning a Bam HI-Sfi I fragment from pUC18-PAI-1.wt plasmid into the same sites in this vector. The Bam HI-Spe I fragment from pGEM-PAI-1.stab and Xba I-Bam HI fragment from pGL3-BASIC™ (Promega) containing SV40 polyadenylation signal sequences were ligated into the Bgl II site of pET2.5 and the resulting plasmid.was designated as pET2.5-PAI-1.stab. A 4.2 kb Bam HI fragment from pET2.5-PAI-1.stab containing −1.4 kb from mET-1 promoter, PAI-1.stab gene, SV40 polyadenylation signal and first exon and first intron of mET-1 gene was cloned into the Bam HI site of p5.9-Luc plasmid replacing the luciferase gene. The final plasmid construct was designated as p5.9-PAI-1.stab (11.6 kb) and it contains 5.9 kb mET-1 promoter-human stable PAI-1 gene with signal peptide-SV40 polyadenylation signal-first exon and intron of mET-1 gene. The orientation and sequences of cloned inserts in this plasmid was confirmed by DNA sequencing.

The 8.4 kb transgenic construct containing the 5.9 kb 5' flanking promoter region-PAI-1-stab-SV40 Poly A signal-first exon and first intron of mPPET-1 was excised from p5.9-PAI-1 with Xho I and Not I enzymes and then purified from low melting agarose gel by extraction of DNA over a spin column (QIAGEN of Valencia, Calif.). Microinjections into the one-cell embryos retrieved from $B_6D_2$ F1 hybrid were done at the Vanderbilt University Transgenic/ES Cell Shared Resources. A $^{32}$P-labelled DNA probe made to SV40 Poly A signal (by REDIPRIME™ labelling kit, Amersham Pharmacia Biotech, Inc., Piscataway, N.J.) was used for Southern blot hybridization of Eco RI and Cla I-digested genomic DNA from tail biopsies in EXPRESSHYB™ solution (Clonetech, Palo Alto, Calif.) to identify the transgenic founder lines.

Determination of PAI-1 Antigen. Blood samples were collected in 1.5 ml microfuge tubes containing 3.8% sodium citrate (pH 5.4) in a 1:9 ratio respectively and blood cells were precipitated at 3000 rpm for 15 minutes at 4° C. and the supernatant was frozen at −70° C. until the time of assay. Tissue samples from mice were frozen in liquid nitrogen within 3 minutes of collection and stored at −80° C. Frozen tissues were homogenized with a polytron in TGH buffer (20 mM HEPES, pH 7.4, 50 mM NaCl, 10% glycerol and 1% Triton X-100 containing a cocktail of protease inhibitors (Roche, Indianapolis, Ind.) on ice (3 pulses of 20 seconds each with 2 minute-intervals of incubaiton on ice). The tissue to TGH buffer ratio was 0.1 g/1.0 ml buffer. The proteins in the homogenized samples were extracted further by mixing on a tilt-board for 10 minutes at 4° C. These samples were spun in a microcentrifuge (14,000 rpm for 10 minutes) at 4° C. The supernatant is transferred to a new tube and frozen and stored at −80° C. PAI-1 antigen levels in samples are determined by using a chromogenic substrate assay kit from Biopool International of Broomfield, Colo. (Cat. #: 211000).

Immunofuctional Assay of PAI-1 Activity. The assay for PAI-1 activity is similar in principle to the method described by Ngo and Declerck (Ngo T H, Declerck P J. Immunological quantitation of rabbit plasminogen activator inhibitor-1 in biological samples. Evidence that rabbit platelets do not contain PAI-1. *Thromb Haemost* 82, 1510–1515, 1999). PAI-1/t-PA complexes are formed by incubating samples with an excess amount of t-PA and then quantitated by a sandwich ELISA method that takes advantage of an anti-PAI-1 monoclonal antibody (MA-21F7) and an anti-t-PA antibody (MA-51H8). The amount of PAI-1/t-PA complexes is dependent on the amount of active PAI-1 in the sample. Recombinant PAI-1-stab protein was used for standard curve where the activity is expressed in ng/ml active PAI-1.

The microtiter plates were coated with a 200 µl of 4.0 µg/ml anti-PAI-1 antibody solution diluted in 1×PBS buffer (pH 7.4) for 48 hrs at 4° C. After removing the excess antibody, the wells were treated for 2 hrs at room temperature with 200 µl of PBS containing 1% bovine serum albumin (BSA). The wells were then washed with 200 µl of PBS containing 0.002% Tween 80 (PBS-Tween) and finally with PBS containing 10% mannitol and 2% saccharose. Samples to be assayed were diluted in PBS-Tween containing 0.1% BSA and 5 mM EDTA (plasma samples should be diluted at least 1:5) and preincubated with an excess of human t-PA (final concentration 20 ng/ml, 37° C. for 25 min). Then, 180 µl of samples were applied to the wells. After incubation for about 18 hours at 4° C. in a moist chamber, the wells were rinsed with PBS-Tween. The plates were filled with 170 µl samples of a horseradish peroxidase (HRP) conjugated monoclonal antibody (MA-51H8, directed against t-PA) diluted with PBS-Tween containing 1 mg/ml BSA, and incubated for 2 hours at room temperature. After repeated washing of the plates, the peroxidase reaction was performed by addition of 160 µl aliquots of a 0.1 M citrate—0.2 M sodium phosphate buffer pH 5.0, containing 300 pg/ml o-phenylenediamine and 0.003% hydrogen peroxide. After 30 min to 1 hr at room temperature, the reaction was stopped with 50 µl of 4 M $H_2SO_4$ and the absorbance at 492 nm was measured.

Histological Analysis and Immunohistochemical Detection of PAI-1. Mice tissues were fixed in 4% paraformaldehyde for overnight followed by embedding in paraffin and sectioning at 5 microns. Sections were deparaffinized before performing the established protocols for hemotoxylin/eosin, Masson's trichrome and Congo Red stainings. Rabbit anti-rat PAI-1 (American Diagnostica, Greenwich, Conn., catalog number 1062) was used for detection of stable PAI-1 antigen. The antigen retrieval was done with RETRIEVIT™ (pH 8.0) reagent (InnoGenex, Inc., San Ramon, Calif.) by microwaving the slides 4 times 5 minutes each. After quenching the endogenous peroxidase activity in 3% $H_2O_2$ solution, the sections were blocked with 10% POWERBLOCK™ solution (BioGenex, Inc., San Ramon, Calif.) which was diluted in 1×PBS buffer containing 0.1% BSA and 0.4% Triton X-100 for 15 minutes. The primary antibody, also diluted in 10% POWERBLOCK™ solution, was added on the sections and incubated at 4° C. for overnight in a humid chamber. The secondary antibody was (biotinylated goat anti-rabbit IgG from Bio Genex, Inc., catalog number HK 394–9R) incubated with the tissue sections for 20 minutes in the humid chamber at the room temperature. The streptavidin-HRP conjugate (InnoGenex, catalog number CJ-1005–50) and the chromogenic substrates diaminobenzidine (DAB) or 3-aminoethyl carbazole (AEC) were used for visualization of immunoreactivity. The sections were counter-stained with hemotoxylin to see the cellular architecture.

RNA Isolation and RT-PCR. Mice tissues were homogenized in RNAzol (0.1 g tissue/ml RNAzol) with a polytron. The RNA from aqueous phase was precipitated with equal volume of isopropanol and washed with 70% ethanol and resuspended in DEPC-treated water. One pg of total RNA was added into the Access RT-PCR (Promega) mix to detect the transcription of PAI-1-stab transgene. The primers used to amplify the 260 bp SV40 Poly A signal were CTA-GAGTCGGGGCGGC (SEQ ID NO:8) for the 5' end and CTTATCGATTTTACCACATTTGTAGAGG (SEQ ID NO:9) for the 3' end of the amplicon.

Example 1

Preparation of Transgenic Mice

PAI-1 is the major physiological inhibitor of plasminogen activation. To explore the impact of chronic overexpression of PAI-1 on vascular pathology, a strain of transgenic mice was developed in which the mice expressed a mutant, conformationally stable, human PAI-1 under the control of the murine preproendothelin-1 promoter. As depicted in FIG. 1, the stable human PAI-1 gene was cloned into a plasmid containing the mouse preproendothelin-1 (mPPET-1) gene promoter (5.9 kb). Xho I-Not I Fragment of p5.9-PAI-1.stab was used for microinjections to generate the transgenic mouse.

Transient transfection of this plasmid into bovine aortic endothelial cells (BAEC) and rat aortic smooth muscle cells (RASM) confirmed the endothelial specificity of this promoter in vitro. Microinjections of 5 ng of PAI-1-stab transgene construct into the one-cell embryos retrieved from $B_6D_2$ F1 hybrid produced 64 live-born pups. Two transgenic founder mice lines were identified by Southern blot hybridization and by determination of PAI-1 antigen levels in the plasma. The copy number of PAI-1-stab transgene was twice as much in Line I as it was in Line II (quantified by PHOSPHORIMAGER™ analysis). The hemizygous animals from founder Line I and Line II had plasma PAI-1 levels of 10.7+3.1 ng/ml (n=6) and 5.5+2.7 ng/ml (n=6) respectively with a p<0.0001 by ANOVA. Due to the higher PAI-1 levels in plasma, the founder Line I was chosen for further characterization.

Example 2

Phenotype of Transgenic Mice

Figure 2:
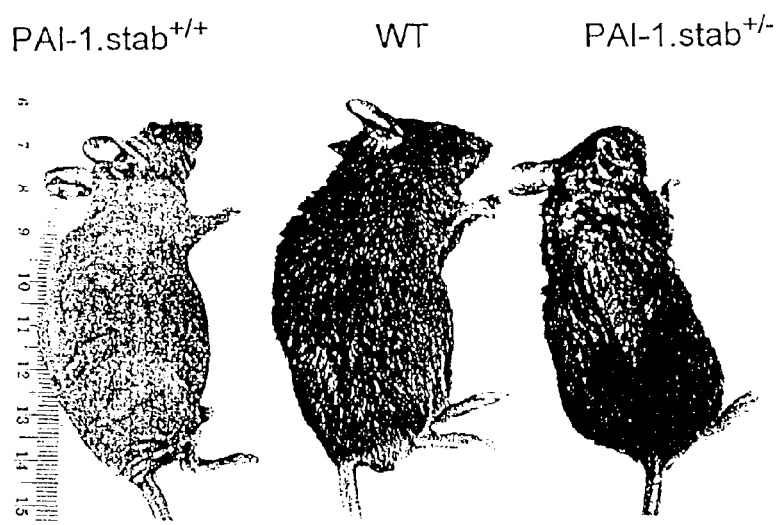
FIG. 2 is a photograph comparing transgenic mice PAI-1.stab +/+ (left) and PAI-1.stab +/− (right), with a wild type mouse (center) to illustrate the extent of epidermal phenotype in the transgenic mice.
Figure 3:
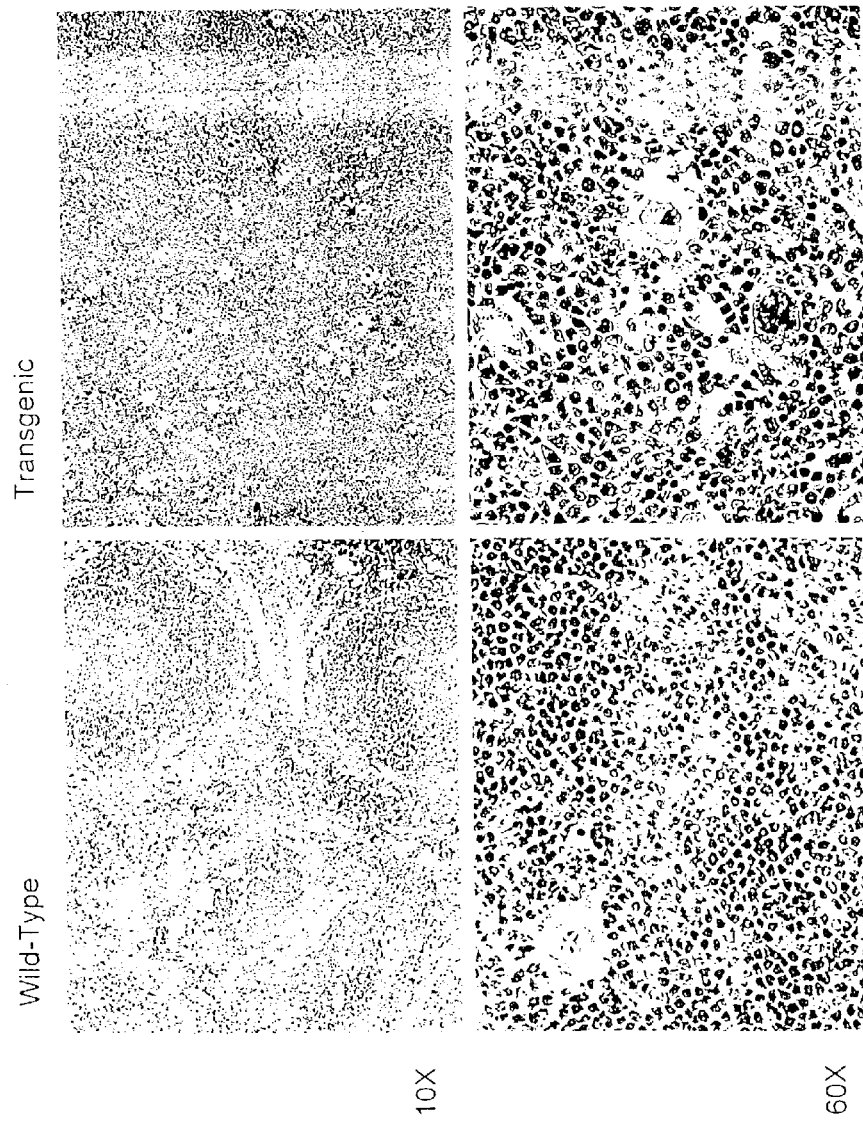
FIG. 3 is a set of photographs comparing hemotoxylin and eosin stained spleen sections from a wild type mouse (left upper and left lower) and a transgenic mouse (right upper and right lower). Upper photographs are at 10×magnification and lower photographs are at 60×magnification.

Transgenic founders and their offspring exhibited a readily detectable and permanent pattern of patchy to complete hair loss that strongly correlated with plasma PAI-1 levels and transgene copy number. PAI-1 ELISA and RT-PCR analyses detected transgene expression in skin, heart, lung, aorta, pancreas, kidney, brain, liver and spleen, as well as in plasma. Transgenic animals also exhibited decreased intraperitoneal fat and splenomegaly (2.91 fold, n=15) compared to wild-type animals. Backcrossed homozygous transgenic animals had an exaggerated phenotype including complete alopecia, absence of subcutaneous fat, hepatosplenomegaly (5.42 fold for spleen, and 1.9 fold for liver, n=6) and fibrotic lesions on the skin and face. See FIGS. 2 and 3. The massive splenomegaly was due to disruption of normal splenic architecture by extramedullary hematopoeisis, while the hepatomegaly reflected increased matrix and amyloid deposition.

Both lines of PAI-1-stab transgenic mice initially displayed a coat with wavy hair and then a pattern of patchy to complete hair loss. Both lines also have no vibrissae with respect to their wild-type littermates. Especially the homozygous animals of Line I 6 to 8 weeks post-partum, begin to lose hair excessively and eventually develop complete alopecia and unusual fibrotic lesions in the skin and face as well as apocrine cysts in the skin. These lesions occasionally became necrotic spots in the skin, where disappearance of epithelium, accumulation of neutrophils, and bacterial growth were observed. The expression of stable PAI-1 gene resulted in striking differences in epidermal morphology of transgenic mice relative to the wild-type animals. Sections from the dorsal, muzzle and tail skin have shown thickening of epidermal layer, reduced hair follicular density and impaired follicular keratinization pattern in transgenic mice. Microscopic analysis indicates that a disorganized keratinization and pigmentation pattern also exists in hair strands of hemizygous transgenic animals. Excessive fibrosis or connective tissue, most probably due to collagen deposits observed in transgenic skin appears to be constraining the hair follicles. The histochemical examination of skin sections showed signs of a reduction in subcutaneous fat relative to the wild-type animal. The screening for Oil Red'O staining intensity confirmed that along with the skin, aorta and liver tissues from transgenic animals have considerably less fat than wild-type tissues. The visceral fat pads were considerably reduced or nonexistent in most transgenic animals.

In addition to the differences in epidermal morphology, the internal organs of transgenic animals were strikingly larger. Spleen and liver of homozygous transgenic mice (n=11) were the most enlarged organs; 6.3 fold for spleen and 1.9 for liver resulting in hepatosplenomegaly developed as a consequence of PAI-1-stab expression. Hepatosplenomegaly is visually noticeable in the live transgenic animals by their puffy abdomen and dark blue spleen seen through the hairless skin. Spleen and liver are followed by enlargement seen in the heart, 1.59 fold, lung, 1.59 fold and the kidney, 1.24 fold.

The structural architecture of spleen has been drastically changed in transgenic mice where red pulp is taken over by white pulp and it contains bone marrow elements such as megacaryocytes, erythroid precursors, nucleated red cells, myeloblast, lymphoids, all of which indicate extramedullary hematopoeisis or a type of lympho-proliferative disease in the spleen. Transgenic spleen tissue was also found to contain fibroid deposits revealed by trichrome stain. Focal and sparse amyloid deposits in the Congo Red stained sections were evident under the polarized light.

Analysis of liver tissues showed that while there is no evidence of extramedullary hematopoeisis, the sinusoids are deposited with a proteinaceious material which appears to surround the hepatocytes. When stained with Congo Red, this proteinaceious deposit in the liver tissue sections yielded an apple green birefringence under the polarized light that is typical of amyloid deposits. Kidneys from transgenic animals appear to have enlarged glomeruli that have more fibrosis relative to the wild-type. Some of the glomeruli in the kidneys from the transgenic mice also have amyloids deposited revealed by the Congo Red stained sections. Histochemical analysis of heart, aorta and brain tissues did not show any remarkable differences as compared to the wild-type.

When bone marrow from transgenic animals were compared to that of wild-type, no striking differences in cellularity, cell size and shape were observed. Interestingly, no fibrosis was present in both hemizygous and homozygous transgenics (n=6). Cellular morphology of bone marrow from transgenic animals did not display any striking differences and looked as heterogenously populated as that of wild-type bone marrow. No statistically significant changes in the systolic or diastolic blood pressure of transgenic mice were observed. It was, however, observed that transgenic animals older than 6 months developed spontaneous coronary arterial thrombosis and subacute myocardial infarction. In addition, lactate dehdrogenase (LDH) enzyme levels in homozygous transgenic mice (n=7) were 40% of and in hemizygous transgenics (n=5) were 60% of the LDH levels detected in the wild-type mice (n=4).

Example 3

Tissue Distribution and Cellular Localization of PAI-1-Stab Expression

Semi-quantitative analysis of total RNA from various organs of transgenic mice by RT-PCR revealed that stable PAI-1 gene was transcribed in heart, aorta, lung and brain at considerably higher levels with residual amount of transcript detected in kidney and liver tissues. Spleen had no detectable stable PAI-1 transcript. PAI-1 ELISA and RT-PCR analyses showed that the pattern of tissue distribution of PAI-1-stab antigen follows that of PAI-1-stab mRNA. The protein extracts from dorsal skin samples had the highest PAI-1 antigen (380 ng/ml) and activity (254 ng/ml) followed by the comparable levels of both antigen (34 ng/ml) and activity (22 ng/ml) detected in the heart tissue. Although, it was difficult to assay PAI-1 activity, the protein extract from the following tissues had detectable levels of PAI-1-stab antigen: pancreas (13 ng/ml), brain tissues (14 ng/ml), lung (40 ng/ml), kidney (12 ng/ml), liver (10 ng/ml) and spleen (5 ng/ml). Activity assays done on plasma suffered from interference when there was no substrate (t-PA) added. Upon correction for this interference, PAI-1 activity in plasma from homozygous transgenic animals was found to be 45 ng/ml, which is in agreement with the observed antigen values.

Immunohistochemical staining of dorsal skin sections localized the expression of human PAI-1 to infundibulum and inner root sheath and outer root sheath cells in the hair follicles of epidermis. Lung tissue was diffusedly stained by anti PAI-1 antibody around the alveoli whereas tracheal epithelia, peribronchial epithelium and especially tracheal columnar epithelium were found to be distinctively positive for PAI-1 antigen. The endothelial cells of microvessels, valve leaflets and aortic sinus of the heart tissue from transgenic mice were also detected by PAI-1 immunostain. In the kidney tissue, the endothelial cells of tubules and microvessels and in liver, the endothelial cells of capillary walls were stained by PAI-1 antibody. Even though trichrome stainings did not show any sign of fibrosis, a heterogeneous population of bone marrow cells appears to express PAI-1 stab protein abundantly as compared to wild type bone marrow.

Discussion of Examples 1–3

Overexpression of a stable form of human PAI-1 produced a pronounced cutaneous phenotype as well as hepatosplenomegaly, extramedullary hematopoeisis in spleen and systemic amyloidosis in mice. These phenotypes are observed in both lines of PAI-1-stab transgenic mice, and severity is strongly correlated with the copy number of the transgene and PAI-1 levels in the plasma. Thus, the observed phenotypes are independent of the transgene integration site but rather a consequence of PAI-1-stab transgene expression.

In order to target PAI-1-stab expression to vascular endothelial cells, the mPPET-1 (5.9 kb) was chosen because it has been reported to yield high levels of luciferase expression and high specificity, though not limited, to endothelial cells of aortic tissue (Harats D, Kurihara H, Belloni P, Oakley H, Ziober A, Ackley D, Cain G, Kurihara Y, Lawn R, and Sigal E, Targeting Gene Expression to the Vascular Wall in Transgenic Mice Using the Murine Preproendothelin-1 Promoter, *J. Clinical Investigation*, 95: 1335–1344, 1995) in vitro and in vivo. The pattern of PAI-1-stab expression in tissues follows that of the luciferase expression in transgenic mice under the control of mPPET-1 promoter despite some differences in relative levels in each organ. The most striking difference is the level of expression that was observed in the skin as the highest versus low levels of luciferase expression observed by Harats et al. in the skin (Harats D, Kurihara H, Belloni P, Oakley H, Ziober A, Ackley D, Cain G, Kurihara Y, Lawn R, and Sigal E, Targeting Gene Expression to the Vascular Wall in Transgenic Mice Using the Murine Preproendothelin-1 Promoter, *J. Clinical Investigation*, 95: 1335–1344, 1995). This difference might be due to different strain of mice and different in vivo stability of luciferase and PAI-1-stab proteins.

The transgenic animals have thickened epidermal layer compared to wild-type littermates and display impaired keratin and pigment organization in the hair strands, thus suggesting that the regulation of keratinocyte growth and differentiation is impaired due to high levels of PAI-1-stab expressed in infundibulum and inner root sheet cells of hair follicles. Thus, the perturbation of extracellular proteolytic balance in epidermal tissue has detrimental effects on self-renewal of epidermis.

The present stable PAI-1 transgenics did not have any swollen limbs or truncated tail. Transgenic animals younger than 6 month old have not displayed any venous or arterial thrombosis as a result of chronicle exposure to this conformationally stable form of human PAI-1. When homozyogus transgenic animals older than 6 month were characterized, it was observed that these animals had developed spontaneous coronary arterial thrombosis in the absence of hyperlipidemia or insulin resistance or hypertension. Systemic amyloidosis was also observed over time in the PAI-1-stab transgenic mice.

Taken together, these findings indicate that PAI-1 influences a broad spectrum of processes involving cellular migration and matrix proteolysis that can impact upon the pathogenesis and treatment of disparate human disorders such as vascular thrombic disorders, asthma, chronic obstructive pulmonary disease, Alzheimer's Disease, myelofibrosis, wasting disorders characterized by weight loss (e.g. anorexia, AIDS, etc.), systemic amyloidosis, alopecia, male pattern baldness, glomerulosclerosis, keloids, apocrine cysts, acne, atherosclerosis, aging, a wound, and combinations thereof.

Example 4

Additional Transgenic Lines

This Example examined whether altering specific functional domains in human PAI-1 would prevent or reduce the extent of coronary arterial thrombosis and other complex phenotypic abnormalities. Two newly engineered lines of transgenic mice were generated (employing techniques similar to those employed in Examples 1–3): one expressing human PAI-1 with impaired RCL (RCL-mutant) and another expressing human PAI-1 with impaired VN binding site (VNBS-mutant). Four (4) founder lines for both RCL- and VNBS-mutant transgenics were identified. Visual inspection of these founders shows that while VNBS-mutant mice display alopecia, RCL-mutant mice have normal hair growth. Hemizygous RCL-mutant and VNBS-mutant transgenic mice have plasma PAI-1 levels of 7.8 and 11.9 ng/ml respectively. Although VNBS-mutants display hepatosplenomegaly and extramedullary hematopoesis to the same extent as mice transgenic for PAI-1 with both functional domains, these phenotypes were negligible in the RCL-mutants. In conclusion, the RCL or the PA inhibitory domain of PAI-1 is critical in yielding the complex phenotypes observed in PAI-1 transgenic mice. These novel findings further support that PAI-1 inhibitors can be employed in the treatment of a broad spectrum of human conditions and disorders, including myelofibrosis, amyloidosis, and hair loss.

REFERENCES

The references listed below (which are also cited herein above by numeral) as well as all references cited in the specification are incorporated herein by reference to the extent that they supplement, explain, provide a background for or teach methodology, techniques and/or compositions employed herein.

1. Sprengers E D, Kluft C. Plasminogen activator inhibitors. Blood 1987; 69: 381–7.
2. Rosenberg R D, Aird W C, 1999. Vascular-bed-specific hemostasis and hypercoagulable states. *New England Journal of Medicine*. 340:1555–1564.
3. Francis R B Jr, Kawanishi D, Baruch T, Mahrer P, Rahimtoola S, Feinstein D I. Impaired fibrinolysis in coronary artery disease. Am Heart J 1988; 115:776–80.
4. Booth N A. Natural inhibitors of fibrinolysis. In Bloom A L, Forbes C D, Thomas D P and Tuddenham E G D (eds) Haemostasis and Thrombosis, $3^{rd}$ edin, pp699–717. Edinburg: Churchill Livingstone, 1994.
5. Loskutoff D J, N Y T, Sawdey M, Lawrence D. Fibrinolytic system of cultured endothelial cells regulation by plasminogen activator inhibitor. Journal of Cellular Biochemistry, 1986; 32:273–80.
6. Samad F, Yamamoto K, Loskutoff D J. Distribution and regulation of plasminogen activator inhibitor-I in murine adipose tissue in vivo. Induction by tumor necrosis factor-alpha and lipopolysaccharide. Journal of Clinical Investigation 1996; 97:37–46.
7. Chomiki N, Henry M, Alessi M C, Anfosso F, Juhan-Vague I. Plasminogen activator inhibitor-I expression in human liver and healthy or atherosclerotic vessel walls. Thrombosis & Haemostasis 1994; 72:44–53.
8. Declerck P J, Alessi M C, Verstreken M, Kruithof E K, Juhan-Vague 1, Collen D. Measurement of plasminogen activator inhibitor I in biologic fluids with a murine monoclonal antibody-based enzyme-linked immunosorbent assay. Blood 1988; 71:220–5.
9. Vaughan D E, Rouleau J-L, Ridker P M, Arnold J M O, Menapace F J, Pfeffer M A. Effects of ramipril on plasma fibrinolytic balance in patients with acute anterior myocardial infarction. Circulation 1997; 96:442–447.
10. Vaughan D E, Declerck P J, Van Houtte E, De Mol M, Collen D. Studies of recombinant plasminogen activator inhibitor-I in rabbits. Pharmacokinetics and evidence for reactivation of latent plasminogen activator inhibitor-I in vivo. *Circulation Research* 1990; 67:1281–6.
11. Keijer J, Ehrlich H J, Linders M, Preissner K T, Pannekoek H. Vitronectin governs the interaction between plasminogen activator inhibitor 1 and tissue-type plasminogen activator. *Journal of Biol. Chem.* 1991; 266:10700–7.
12. Emeis J J, Kooistra. T. Interleukin I and lipopolysaccharide induce an inhibitor of tissue-type plasminogen activator in vivo and in cultured endothelial cells. *Journal of Experimental Medicine* 1986; 163:1260–6.
13. Sawdey M, Podor T J, Loskutoff D J. Regulation of type I plasminogen activator inhibitor gene expression in cultured bovine aortic endothelial cells. Induction by transforming growth factor-beta, lipopolysaccharide, and tumor necrosis factor-alpha. *Journal of Biological Chemistry* 1989; 264:10396–401.
14. Dichek D, Quertermous T. Thrombin regulation of mRNA levels of tissue plasminogen activator and plasminogen activator inhibitor-I in cultured human umbilical vein endothelial cells. *Blood* 1989; 74:222–8.
15. Alessi M C, Juhan-Vague 1, Kooistra T, Declerck P J, Collen D. Insulin stimulates the synthesis of plasminogen activator inhibitor I by the human hepatocellular cell line HepG2. *Thrombosis & Haemostasis* 1988; 60:491–4.
16. Colucci M, Paramo J A and Collen D. Generation in plasma of a fast-acting inhibitor of plasminogen activator in response to endotoxin stimulation. *J. Clin Invest* 1985; 75: 818–24.
17. Vaughan D E, Lazos S A, Tong K. Angiotensin II regulates the expression of plasminogen activator inhibitor-I in cultured endothelial cells. A potential link between the renin-angiotensin system and thrombosis. *Journal of Clinical Investigation* 1995; 95:995–1001.
18. Feener E P, Northrup J M, Aiello L P, King G L. Angiotensin II induces plasminogen activator inhibitor-I and -2 expression in vascular endothelial and smooth muscle cells. *Journal of Clinical Investigation* 1995; 95:1353–62.
19. Aertgeerts K, De Bondt H L, De Ranter C, Declerck P J. A model of the reactive form of plasminogen activator inhibitor-1. *Journal of Structural Biology* 1994; 113:239–45.
20. Kruithof E K; Tran-Thang C, Ransijn A, Bachmann F. Demonstration of a fast-acting inhibitor of plasminogen activators in human plasma. *Blood* 1984; 64:907–13.
21. Declerck P J, De Mol M, Alessi M C, et al. Purification and characterization of a plasminogen activator inhibitor I binding protein from human plasma. Identification as a multimeric form of S protein (vitronectin). *Journal of Biological Chemistry* 1988; 263:15454–61.
22. M. B. Berkenpas, D. A. Lawrence and D. Ginsburg. Molecular evolution of plasminogen activator-1 functional stability, *EMBO J.* (1995) 14: 2969–2977.
23. Wiman B, Ljungberg B, Chmielewska J, Urden G, Blomback M, Johnsson H. The role of the fibrinolytic system in deep vein thrombosis. *J Lab Clin Med* 1985; 105:265–70.
24. Auwerx J, Bouillon R, Collen D, Geboers J. Tissue-type plasminogen activator antigen and plasminogen activator inhibitor in diabetes mellitus. *Arteriosclerosis* 1988; 8:68–72.
25. Margaglione M, Di Minno G, Grandone E, et al. Abnormally high circulation levels of tissue plasminogen activator and plasminogen activator inhibitor-1 in patients with a history of ischemic stroke. *Arterioscler Thromb* 1994; 14:1741–5.
26. Thogersen A M, Jansson J H, Boman K, et al. High plasminogen activator inhibitor and tissue plasminogen activator levels in plasma precede a first acute myocardial infarction in both men and women: evidence for the fibrinolytic system as an independent primary risk factor. *Circulation* 1998; 98:2241–7.
27. Juhan-Vague 1, Valadier J, Alessi M C, et al. Deficient t-PA release and elevated PA inhibitor levels in patients with spontaneous or recurrent deep venous thrombosis. *Thrombosis & Haemostasis* 1987; 57:67–72.
28. Harats D, Kurihara H, Belloni P, Oakley H, Ziober A, Ackley D, Cain G, Kurihara Y, Lawn R, and Sigal E, Targeting Gene Expression to the Vascular Wall in Transgenic Mice Using the Murine Preproendothelin-1 Promoter, *J. Clinical Investigation,* 95: 1335–1344,1995.
29. Ngo T H, Declerck P J. Immunological quantitation of rabbit plasminogen activator inhibitor-1 in biological samples. Evidence that rabbit platelets do not contain PAI-1. *Thromb Haemost* 82, 1510–1515, 1999.
30. Romer J, Lund L R, Eriksen J, Pyke C, Kristensen P. and Dano K, The receptor for urokinase-type plasminogen activator is expressed by keratinocytes at the leading edge during re-epithelialization of mouse skin wounds, *J Invest Dermatol.,* 102: 519–522, 1994.
31. Grondahl-Hansen J, Lund L R, Ralfkiaer E, Ottevanger V, and Dano K, Urokinase- and tissue-type plasminogen activators in keratinocytes during wound reepithelization in vivo, *J Investigative Dermatol.,* 1988.
32. Jensen P J and Lavker R M, Modulation of the plasminogen activator cascade during enhanced epidermal proliferation in vivo, *Cell Growth Differ.* 7: 1793–804, 1996.
33. Jensen P J, and Lavker R M, Urokinase is a positive regulator of epidermal proliferation in vivo, *J Invest Dermatol.* 112: 240–4, 1999.
34. T. Shimomura, J. Kondo, M. Ochiai, D. Naka, K. Miyazawa, Y. Morimoto and N. Kitamura, Activation of the zymogen of hepatocyte growth factor activator by thrombin. *J. Biol. Chem.* 268 (1993), 22927–22932.
35. Lee Y R, Yamazaki M, Mitsui S, Tsuboi R, Ogawa H. Hepatocyte growth factor (HGF) activator expressed in hair follicles is involved in in vitro HGF-dependent hair follicle elongation. *J Dermatol Sci.* 2001 Feb;25(2): 156–63.
36. Zhou H M, Nichols A, Meda P and Vassalli J D, Urokinase-type plasminogen activator and its receptor synergize to promote pathogenic proteolysis, *EMBO J,* 19: 4817–4826, 2000.
37. Erickson L A, Fici G J, Lund E J, Boyle T P, Polites H G, Marotti K R, Development of venous occlusion in mice transgenic for the PAI-1, *Nature,* 346: 74–76, 1990.
38. Michael Tucker, Muthoni Kihiko, Joseph N. Caldwell, Sarah Wright, Takeshi Kawarabayashi, Douglas Price, Donald Walker, Stephen Scheff, Joseph P. McGillis, Russell E. Rydel, and Steven Estus The Plasmin System Is Induced by and Degrades Amyloid-β Aggregates *J. Neurosci.* 20: 3937–3946, 2000.
39. Van Nostrand W E and Porter M, Plasmin Cleavage of the Amyloid β-Protein: Alteration of Secondary Structure and Stimulation of Tissue Plasminogen Activator Activity, *Biochemistry,* 38: 11570–11576, 1999.

It will be understood that various details of the invention can be changed without departing from the scope of the invention. Furthermore, the foregoing description is for the purpose of illustration only, and not for the purpose of limitation—the invention being defined by the claims.

What is claimed is:

1. A transgenic mouse having incorporated into its genome a plasminogen activator inhibitor-1 (PAI-1) gene encoding a biologically active PAI-1 polypeptide operably linked to a murine preproendothelin-1 promoter, the PAI-1 gene being present in said genome in a copy number effective to confer overexpression in the transgenic mouse of the PAI-1 polypeptide resulting in a phenotype selected from the group consisting of alopecia, absence of subcutaneous fat, hepatosplenomegaly, skin fibrotic lesions, facial fibrotic lesions, age-dependent spontaneous coronary arterial thrombosis, and combinations thereof.

2. A method of testing a candidate composition for PAI-1 inhibition activity, the method comprising:
 (a) obtaining a transgenic mouse having incorporated into its genome a plasminogen activator inhibitor-1 (PAI-1) gene encoding a biologically active PAI-1 polypeptide operably linked to a murine preproendothelin-1 promoter, the PAI-1 gene being present in said genome in a copy number effective to confer overexpression in the transgenic mouse of the PAI-1 polypeptide resulting in a phenotype selected from the group consisting of alopecia, absence of subcutaneous fat, hepatosplenomegaly, skin fibrotic lesions, facial fibrotic lesions, age-dependent spontaneous coronary arterial thrombosis, and combinations thereof;

(b) admInistering a candidate composition to the transgenic mouse; and (c) observing the transgenic mouse in step (b), wherein an ameliorating change in the phenotype of the transgenic mouse is indicative of inhibition of the activity of PAI-1.

3. A transgenic mouse having incorporated into its genome a plasminogen activator inhibitor-1 (PAI-1) gene encoding a biologically active PAI-1 polypeptide operably linked to a murine preproendothelin-1 promoter, the PAI-1 gene being present in said genome in a copy number effective to confer overexpression in the transgenic mouse of the PAI-1 polypeptide resulting in alopecia.

4. The transgenic mouse of claim 3, wherein the PAI-1 gene is further defined as comprising a human PAI-1 polypeptide-encoding nucleic acid segment.

5. The transgenic mouse of claim 3, wherein the expression of the PAI-1 polypeptide is conferred in hair-producing tissue of the transgenic mouse.

6. A method of testing a candidate composition for PAI-1 inhibition activity, said method comprising:

(a) obtaining a transgenic mouse having incorporated into its genome a plasminogen activator inhibitor-1 (PAI-1) gene encoding a biologically active PAI-1 polypeptide operably linked to a murine preproendothelin-1 promoter, the PAI-1 gene being present in said genome in a copy number effective to confer overexpression in the transgenic non-human animal of the PAI-1 polypeptide resulting in alopecia;

(b) administering the composition to the transgenic mouse; and (c) observing the transgenic mouse in step (b), wherein an ameliorating change in the transgenic mouse indicative of inhibition of the activity of PAI-1, wherein the ameliorating change is selected from the group consisting of hair growth, a reduction of hair loss, prevention of hair loss, and combinations thereof.

7. The method of claim 6, wherein the PAI-1 gene is further defined as comprising a human PAI-1 polypeptide-encoding nucleic acid segment.

8. The method of claim 6, wherein the expression of the PAI-1 polypeptide is conferred in hair-producing tissue of the transgenic mouse, and the change indicative of inhibition of PAI-1 activity is observed in the hair-producing tissue.

* * * * *